US008975288B2

(12) United States Patent
Keiler et al.

(10) Patent No.: US 8,975,288 B2
(45) Date of Patent: Mar. 10, 2015

(54) F2 DERIVATIVES AS ANTIBACTERIAL AGENTS

(71) Applicants: Kenneth Charles Keiler, Boalsburg, PA (US); John Nandwa Alumasa, State College, PA (US)

(72) Inventors: Kenneth Charles Keiler, Boalsburg, PA (US); John Nandwa Alumasa, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 12 days.

(21) Appl. No.: 13/833,976

(22) Filed: Mar. 15, 2013

(65) Prior Publication Data

US 2014/0275192 A1 Sep. 18, 2014

(51) Int. Cl.
*C07D 257/06* (2006.01)
*A01N 43/713* (2006.01)

(52) U.S. Cl.
CPC ............ *C07D 257/06* (2013.01); *A01N 43/713* (2013.01)
USPC .......................................... 514/381; 548/251

(58) Field of Classification Search
None
See application file for complete search history.

(56) References Cited

U.S. PATENT DOCUMENTS 4,419,357 A 12/1983 Peet et al.
4,764,525 A 8/1988 Connor et al.

FOREIGN PATENT DOCUMENTS

WO WO 2004/101532 11/2004

OTHER PUBLICATIONS

McGillivray et al., *Antimicrob Agents Ch* 56(4):1854-1861 (Apr. 2012).
Wo 2013/154,793 International Search Report Jul. 29, 2013.

*Primary Examiner* — Alicia L Otton
(74) *Attorney, Agent, or Firm* — Husch Blackwell, LLP

(57) ABSTRACT

A compound or its pharmaceutically acceptable salt, as well as a pharmaceutical, composition containing that compound or salt dissolved or dispersed in a pharmaceutically acceptable carrier, and a method of using that compound or salt in an antibacterial treatment. A contemplated compound corresponds in structure to structural Formula I or a pharmaceutically acceptable salt of that compound, wherein V is O or $NR^9$, Y is halogen, $OR^{10}$, $C_1$-$C_4$ hydrocarbyl or $NHR^{10}$, Z is $NR^2$—X—$R^1$ or $CH_2$—$R^8$, n is 1-6, X is H, $S(O)_2$, C(O), C(O)$NR^7$, C(NH)$NR^7$ or C(O)O, and $R^1$, $R^2$, $R^7$, $R^8$, $R^9$ and $R^{10}$ are defined within.

I

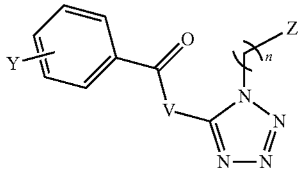

23 Claims, 4 Drawing Sheets

F2 DERIVATIVES AS ANTIBACTERIAL AGENTS

CROSS-REFERENCE TO RELATED APPLICATION

This application claims priority of provisional application Ser. No. 61/622,163 filed on Apr. 10, 2012, and whose disclosures are incorporated by reference.

FIELD OF INVENTION

The invention relates to antibacterial agents and to their use. More particularly, the invention relates to N-(1-(2-aminoethyl)-1H-tetrazol-5-yl)-3-chlorobenzamide and its amido, sulfonamide, urea and urethane derivatives, their use in the preparation of a pharmaceutical composition and as a bactericide and bacteriostat.

BACKGROUND ART

It is estimated that 20% of newly synthesized proteins are degraded by the proteosome due to transcriptional or translational errors [Wickner et al., Science 286:1888-1893 (1999)] and this number increases under stress conditions such as heat shock [Wickner et al., *Science* 286:1888-1893 (1999); Ingmer et al., *Res Microbiol* 160:704-710(2009)]. Bacterial proteosomes also control the half-life of transcription factors and rate-limiting enzymes thereby exerting a regulatory effect on gene expression and metabolism. Thus, regulated proteolysis is critical from a quality control as well as a regulatory standpoint and loss of these intracellular proteases can have detrimental effects [Frees et al., *Mol Microbiol* 63:1285-1295 (2007); Jenal et al., *Curr Opin Microbiol* 6:163-172 (2003)]

During infection, pathogens face numerous stress conditions including nutrient deprivation, exposure to reactive oxygen species, temperature and pH changes. Loss of the caseinolytic protease (Clp) system attenuates virulence in several pathogens including *B. anthracis* and *S. aureus* [Frees et al., *Mol Microbiol* 63:1285-1295 (2007); Ingmer et al., *Res Microbiol* 160:704-710 (2009); McGillivray et al., *J Innate Immun* 1:494-506 (2009)] making the ClpXp protease a potential target for pharmacological intervention.

Caseinolytic proteases (Clp; EC 3.4.21.92) are endopeptidase enzymes of peptidase family S14 originally obtained from bacteria. Clp enzymes contain subunits of two types, ClpP, with peptidase activity, and ClpA or ClpX, that exhibit ATPase activity, autonomous chaperone activity and can catalyze protein unfolding These enzymes are intracellular proteases that regulate protein quality and turnover through controlled proteolysis. Degraded proteins include damaged or non-functional proteins as well as transcriptional regulators, rate-limiting enzymes, and proteins tagged during trans-translation [Frees et al., *Microbiol* 63:1285-1295 (2007); Ingmer et al., *Res Microbiol* 160:704-710 (2009); Keiler et al., Annu *Rev Microbiol* 62:133-151 (2008)]. The enzymes hydrolyze proteins to small peptides in the presence of ATP and $Mg^{2+}$. α-Casein is the usual test substrate. In the absence of ATP, only oligopeptides shorter than five residues are hydrolyzed.

Clp protease proteolytic core, ClpP is paired with a regulatory ATPase such as CLpA or ClpX. Clp ATPases recognize, unfold and transfer the proteins to ClpP for degradation. Orthologs of ClpXp are found in many bacterial species and are often associated with cellular stress such as heat shock, nutrient deprivation, and oxidative stress [Frees et al., *Microbiol* 63:1285-1295 (2007); Ingmer et al., *Res Microbiol* 160:704-710 (2009)]. ClpX and/or ClpP have also been implicated in virulence of several pathogens including *Listeria monocytogenes, Salmonella, Staphylococcus aureus*, and *Streptococcus pneumoniae* [Frees et al., *Microbiol* 63:1285-1295 (2007); Ingmer et al., *Res Microbiol* 160:704-710 (2009)].

The trans-translation mechanism is a key component of multiple quality control pathways in bacteria that ensure proteins are synthesized with high fidelity in spite of challenges such as transcription errors, mRNA damage, and translational frameshifting. trans-Translation is performed by a ribonucleoprotein complex composed of tmRNA, a specialized RNA with properties of both a tRNA and an mRNA, and the small protein SmpB. tmRNA-SmpB interacts with translational complexes stalled at the 3' end of an mRNA to release the stalled ribosomes and target the nascent polypeptides and mRNAs for degradation. In addition to quality control pathways, some genetic regulatory circuits use trans-translation to control gene expression. Diverse bacteria require trans-translation when they execute large changes in their genetic programs, including responding to stress, pathogenesis, and differentiation.

The compound F2, below, was identified as

F2

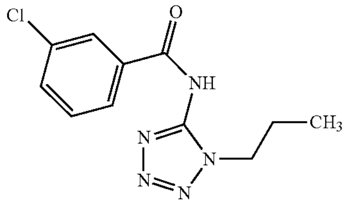

part of a high-throughput screen for inhibitors of the protein-tagging and trans-translation degradation pathway in *E. coli*. F2 has been found to inhibit the activity of ClpXp protease of bacterial cells with minimal host cell cytotoxicity [McGillivray et al., *J Innate Immun* 1:494-506 (2009)]. Although it is unclear exactly how F2 inhibits the ClpXp protease, the data indicate that inclusion of F2 decreases the proteolysis of ClpXp substrates in vivo. Similar to a genetic loss of ClpX, co-treatment of *B. anthracis* with F2 increased susceptibility of the bacteria to cathelicidin antimicrobial peptides. A similar effect was seen with both methicillin-susceptible and methicillin-resistant strains of *S. aureus* suggesting ClpXp also plays a role in cathelicidin resistance in *S. aureus*. The McGillivray et al. paper is the first study to show that inhibition of ClpXp could result in a synergistic interaction with innate immune defenses.

In that paper, McGillivray and co-workers demonstrated that ClpX is critical for the pathogenesis of *Bacillus anthracis*, a Gram-positive bacterium that is the causative agent of anthrax [*J Innate Immun* 1:494-506 (2009)]. Loss of ClpX increased susceptibility to innate host defenses including cationic antimicrobial peptides and severely attenuated *B. anthracis* virulence even in the fully pathogenic Ames strain. Ibid.

Although McGillivray et al. focused upon cathelicidins in that study, they had previously shown loss of ClpX renders *B. anthracis* more sensitive to other antimicrobial proteins, including defensins and lysozyme [McGillivray et al., *J Innate Immun* 1:494-506 (2009)]. Therefore, pharmacological inhibition of ClpXp may increase susceptibility to multiple host defenses.

F2 also sensitizes *B. anthracis* and *S. aureus* to antibiotics such as penicillin and daptomycin, although the synergistic effect between F2 and antibiotics was more pronounced in *B. anthracis*. That enhancement may reflect the assay conditions or it may indicate that the extent to which ClpXp influences susceptibility to cell-envelope antibiotics differs among species.

Evidence of a connection between Clp proteases and cell-wall acting antibiotics has been seen in other bacterial species. Loss of ClpP in *Streptococcus mutans* rendered the bacteria more susceptible to the cell wall acting antibiotics bacitracin, polymyxin B, and vancomycin, although no effect was seen with non-cell wall acting antibiotics [Chattoraj et al., *J Bacteriol* 192:1312-1323 (2010)].

In *Mycobacterium tuberculosis*, loss of the ClpCP protease, another ATPase chaperone, resulted in increased susceptibility to cell wall stress induced by vancomycin or SDS [Barik et al., *Mol Microbiol* 75:592-606 (2010)]. Daptomycin is believed to function by membrane depolarization but a recent study demonstrated that it also induces the cell wall stress regulon including Clp family members in *S. P aureus* [Muthaiyan et al., *Antimicrob Agents Chemother* 52:980-990 (2008)].

The importance of the ClpXp system is further highlighted by those workers' observation that inhibition increased susceptibility to daptomycin in otherwise non-susceptible strains. However, this suppression of resistance was only partial, indicating that non-Clp-dependent effects probably also contribute to daptomycin resistance. It is likely that loss of ClpXp has pleiotropic effects on the bacterial cell because the Clp protease regulates a wide range of genes [Michel et al., *J Bacteriol* 188:5783-5796 (2006); Robertson et al., *J Bacteriol* 184:3508-3520 (2002)].

Cell wall active agents are believed to increase damaged or mis-folded proteins and result in induction of genes involved in protein turnover such as chaperones and proteases [[Muthaiyan et al., *Antimicrob Agents Chemother* 52:980-990 (2008); Utaida et al., *Microbiology* 149:2719-2732 (2003)]. Loss of ClpXp could hamper this response. The ClpXp protease may also be regulating critical components of the cell wall. In *E. coli*, ClpXp can degrade FtsZ, a major cytoskeletal protein that is implicated in cell division and cell wall synthesis [Camberg et al., *Proc Natl Acad Sci USA* 106:10614-10619 (2009)]. In *B. subtilis*, MurAA, an enzyme important in peptidoglycan formation, is degraded by ClpCP [Kock et al., *Mol Microbiol* 51:1087-1102 (2004)].

It is also possible that cell charge is affected by loss of ClpXp. Daptomycin is an anionic compound that associates with calcium to form a cationic complex similar to an antimicrobial peptide. Resistance to daptomycin and cationic antimicrobial peptides has been linked to mutations in mprF (lysine addition to cell membrane phosphatidyl glycerol) and the dltABCD operon (alanylation of cell wall teichoic acids) that result in increased net positive surface charge in both *S. aureus* and *B. anthracis* [Fisher et al., *J Bacteriol* 188:1301-1309 (2006); Kraus et al., *Curr Top Microbiol Immunol* 306:231-250 (2006); Samant et al., *J Bacteriol* 191:1311-1319 (2009); Yang et al., *Antimicrob Agents Chemother* 53:2636-2637 (2009)].

Consistent with this hypothesis, increasing daptomycin resistance in *S. aureus* was accompanied by increased resistance to cationic antimicrobial peptides such as alpha-defensin HNP-1 and platelet microbicidal proteins [Jones et al., *Antimicrob Agents Chemother* 52:269-278 (2008)]. The Clp protease could be regulating expression either directly or indirectly of the mprF or the dltABCD operon although this has not yet been demonstrated.

The ClpXp protease is a promising target for pharmacological intervention. Inclusion of F2 increased the effectiveness of bacterial killing by human whole blood indicating this compound can augment innate immune defenses. This therapeutic effect may be magnified at tissue sites of infection where high levels of antimicrobial peptides are produced by cells such as keratinocytes, and in patients receiving concurrent antibiotic therapy with cell wall active agents for which ClpXp inhibition also provides synergism.

Although McGillivray et al. focused on inhibition of ClpXp, uncontrolled activation of ClpP through a new class of antibiotics, acyl depsipeptides, also has lethal consequences for several bacterial species tested [Brotz-Oesterhelt et al., *Nat Med* 11:1082-1087 (2005)]. However, as was seen with acyl depsipeptides [Brotz-Oesterhelt et al., *Nat Med* 11:1082-1087 (2005)] and other antimicrobial compounds, potential for bacterial resistance to F2 exists. The mechanism behind this resistance is at this point unclear, but it may necessitate that F2 or another pharmacological inhibitor of ClpXp be used in a combination rather than single therapy to limit resistance. Nevertheless, the use of Clp inhibitors can be predicted to contribute to antimicrobial activity on multiple levels, through increased susceptibility to innate immune defenses and decreased resistance to traditional antibiotics, potentially increasing therapeutic effectiveness.

An alternative strategy in antimicrobial therapy is to target and inactivate bacterial virulence factors rather than directly targeting growth or survival in the manner of traditional antibiotics [Cegelski et al., *Nat Rev Microbiol* 6:17-27 (2008)]. Inhibition of virulence factors involved in disease progression should enhance the ability of the host immune system to clear the pathogen. The ClpXp protease is a promising target for pharmacological inhibition due to its conserved nature and its role in the virulence of a wide-variety of pathogens.

A present inventor and colleagues have identified several inhibitors of ClpXp using a screening system devised in *E. coli* [Cheng et al., *Protein Sci* 16:1535-1542 (2007)]. The ClpXp protease of the Gram positive *B. anthracis* Sterne and the Gram positive human pathogen, *Staphylococcus aureus* were targeted using the F2 inhibitor. It was found that F2 renders both *B. anthracis* Sterne and drug-resistant strains of *S. aureus* more susceptible to host antimicrobial peptides as well as antibiotics that target the bacterial cell envelope including the cell wall and/or cell membrane.

BRIEF SUMMARY OF THE INVENTION

The present invention contemplates a compound, as well as a pharmaceutical composition containing that compound. Also contemplated is a method of using that compound as a bacteriostatic or bactericidal treatment for bacteria, and particularly for Gram positive bacteria such as *B. anthracis, B. subtilis, S. mutans, M. tuberculosis* and *S. aureus.*

A contemplated compound of the invention corresponds in structure to structural Formula I or a pharmaceutically acceptable salt of that compound

I

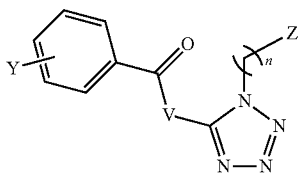

wherein V is O or $NR^9$, Y is halogen, $OR^{10}$, $C_1$-$C_4$ hydrocarbyl or $NHR^{10}$, Z is $NR^2$—X—$R^1$ or $CH_2$—$R^8$, and n is a numeral that is 1-6. In a compound of Formula I, X is hydrido (H), $S(O)_2$, C(O), $C(O)NR^7$, $C(NH)NR^7$ or C(O)O, with the proviso that when X is H, $R^1$ and $CH_2$—$R^8$ are absent. Preferably, X is other than H, and is $S(O)_2$ or C(O). $R^9$ is hydrido (H) or $C_1$-$C_4$ hydrocarbyl; and $R^{10}$ is hydrido or $C_1$-$C_4$ hydrocarbyl. $R^1$ and $R^8$ are the same or different and are an aliphatic, aromatic or heteroaromatic ring system containing one ring or two fused rings each having 5-7 atoms in the ring. The ring system contains up to three substituents other than hydrogen that themselves can be the same or different ($R^{1a}$, $R^{1b}$, and $R^{1c}$). Each of those three groups, $R^{1a-c}$, is separately selected from the group consisting of $C_1$-$C_6$ hydrocarbyl, $C_1$-$C_6$ hydrocarbyloxy, $C_1$-$C_6$ hydrocarbyloxycarbonyl, trifluoromethyl (—$OCF_3$), trifluoromethoxy (—$OCF_3$), $C_1$-$C_7$ hydrocarboyl (acyl), hydroxy-, halogen, halogen-substituted $C_1$-$C_7$ hydrocarboyl, $C_1$-$C_6$ hydrocarbylsulfonyl, $C_1$-$C_6$ hydrocarbyloxysulfonyl, nitro, phenyl, benzyl, cyano, carboxyl, $C_1$-$C_7$ hydrocarbyl carboxylate [C(O)O—$C_1$-$C_7$ hydrocarbyl], carboxamide [$C(O)NR^3R^4$] or sulfonamide [$S(O)_2NR^3R^4$] wherein the amido nitrogen in either group has the formula $NR^3R^4$ in which $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N═N— and Ar is a single-ringed aryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur. $R^2$ and $R^7$ are the same or different and are hydrido (H) or $C_1$-$C_4$ hydrocarbyl.

A preferred compound of Formula I is a compound that corresponds in structure to structural Formula II, below, or a pharmaceutically acceptable salt of that compound

II

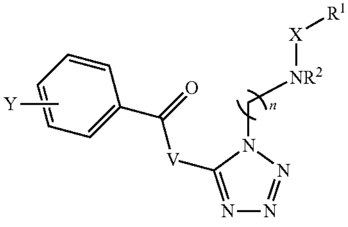

in which V, X, Y, n, $R^1$ and $R^2$ are as defined above. Thus, in Formula II, X is $S(O)_2$, C(O), $C(O)NR^7$, $C(NH)NR^7$ or C(O) O. $R^1$ is an aliphatic, aromatic or heteroaromatic ring system containing one ring or two fused rings each having 5-7 atoms in the ring. The ring system contains up to three substituents other than hydrogen that themselves can be the same or different ($R^{1a}$, $R^{1b}$, and $R^{1c}$). Each of those three groups, $R^{1a-c}$, is separately selected from the group consisting of $C_1$-$C_6$ hydrocarbyl, $C_1$-$C_6$ hydrocarbyloxy, $C_1$-$C_6$ hydrocarbyloxycarbonyl, trifluoromethyl (—$CF_3$), trifluoromethoxy (—$OCF_3$), $C_1$-$C_7$ hydrocarboyl (acyl), hydroxy-, halogen, halogen-substituted $C_1$-$C_7$ hydrocarboyl, $C_1$-$C_6$ hydrocarbylsulfonyl, $C_1$-$C_6$ hydrocarbyloxysulfonyl, nitro, phenyl, cyano, carboxyl, $C_1$-$C_7$ hydrocarbyl carboxylate [C(O)O—$C_1$-$C_7$ hydrocarbyl], carboxamide [$C(O)NR^3R^4$] or sulfonamide [$S(O)_2NR^3R^4$] wherein the amido nitrogen in either group has the formula $NR^3R^4$ in which $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N═N— and Ar is a single-ringed aryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur. $R^2$ and $R^7$ are the same or different and are hydrido (H) or $C_1$-$C_4$ hydrocarbyl.

In preferred practice, n is 2-4. Most preferably n is 2 so that a particularly preferred compound corresponds in structure to Formula IIA, below, wherein X is other than, $R^1$ and $R^2$ are as defined above

IIA

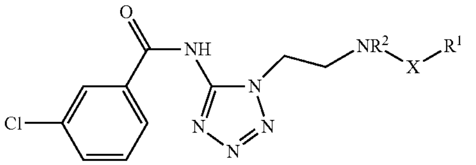

A pharmaceutical composition that contains an antibacterial amount and preferably an antibacterial amount of a compound or its pharmaceutically acceptable salt of Formula I, above, dissolved or dispersed in a pharmaceutically acceptable. diluent is also contemplated.

A method of inhibiting the growth of bacteria is another aspect of the invention. That method contemplates the steps of contacting the bacteria with an antibacterial amount of a compound of Formula I or its pharmaceutically acceptable salt. In some embodiments, the contacted bacterium is *B. anthracis*, whereas in other embodiments the bacterium is *B. subtilis, S. aureus, M. tuberculosis* and *S. mutans* or yet another preferably Gram positive bacterium. In other embodiments, Gram negative bacteria are the contemplated targets.

In some embodiments, the bacteria are present in a cell culture, whereas in other embodiments, the bacteria are present in an infected mammal and the bacteria are contacted by administration of the compound to the infected mammal. Typically, and preferably when the bacteria are present in an infected mammal, the bacteria are contacted a plurality of times.

Also contemplated is another method of inhibiting the growth of bacteria, both Gram positive and Gram negative bacteria. In this method, the bacteria are contacted with a synergistic amount of a compound Formula I or its pharmaceutically acceptable salt and also a synergistic amount of a) a human cathelicidin antimicrobial peptide LL-37 or b) an antibiotic that targets the cell wall and/or the cell membrane.

A particularly preferred compound of Formulas I and II has structural Formula III, below.

III

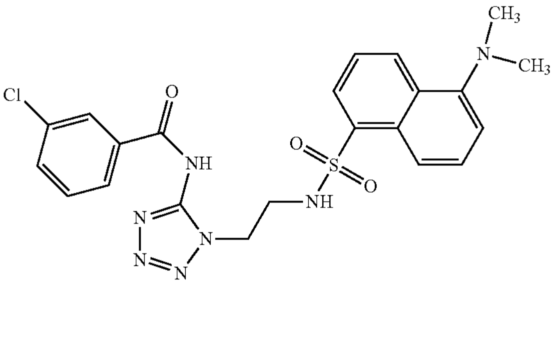

A pharmaceutically acceptable salt of a compound of Formula III is also contemplated. A compound of Formula III is often referred to herein as Dansyl-F2.

BRIEF DESCRIPTION OF THE DRAWINGS

In the drawings forming a part of this disclosure.

DEFINITIONS

Figures 1, 1A:
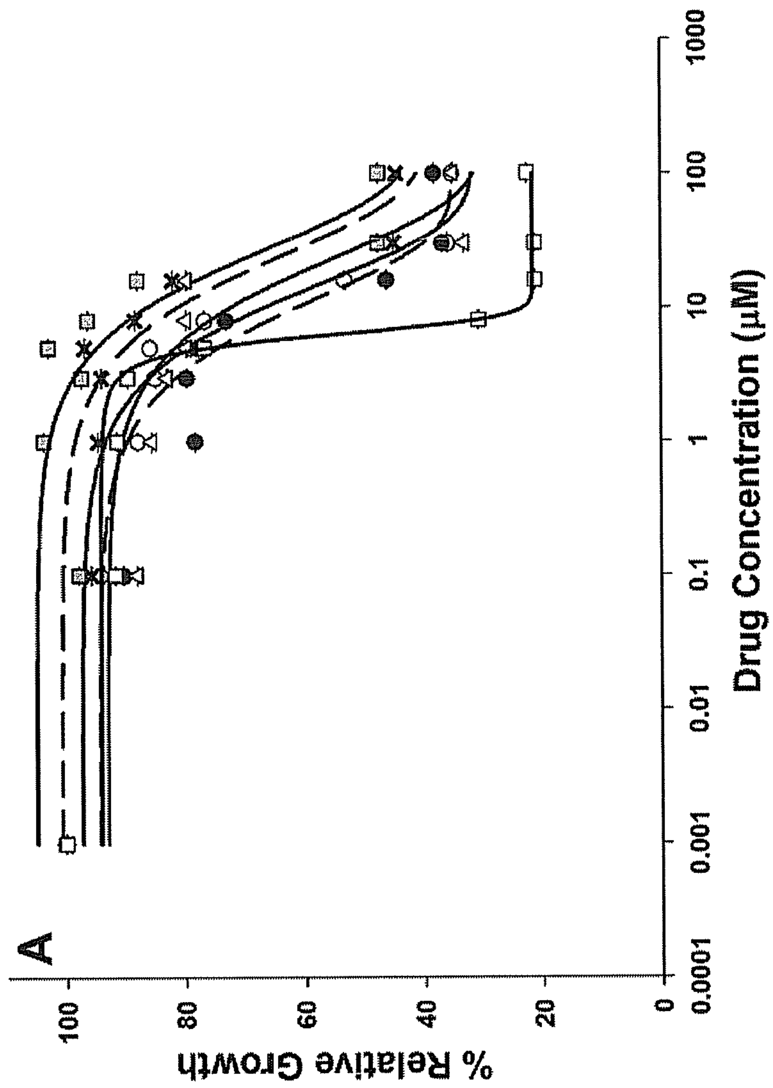
FIG. 1, in two panels as FIG. 1A and FIG. 1B, illustrate dose response analyses of F2 (FIG. 1A) and Dansyl-F2 (FIG. 1B; Formula III) against *B. anthracis* constructs and *S. flexneri*. Strains: WT *B. anthracis* (open circles); ΔclpX (×); ΔclpX+pclpX (filled circles); WT+pUTE29 (empty vector, filled squares); ΔclpX+pUTE29 (open triangles); *S. flexneri* (open squares).
Figure 1B:
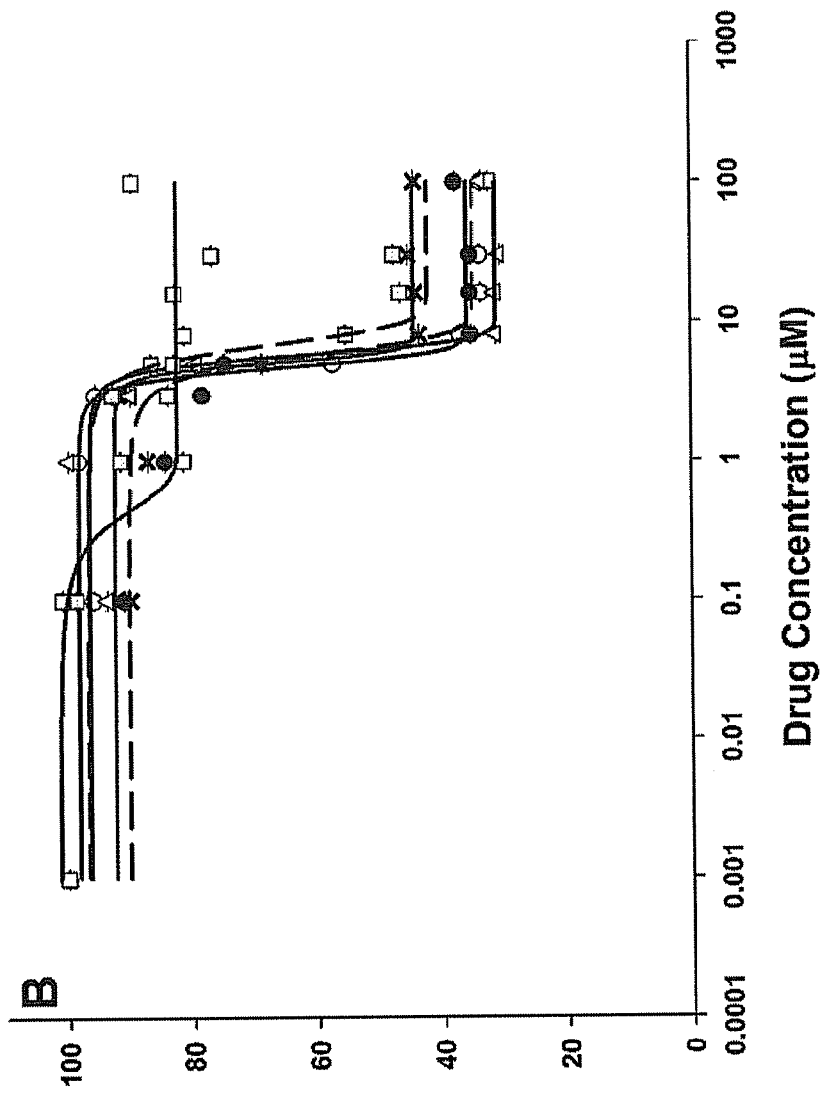

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

As used herein, the term "hydrocarbyl" is a short hand term for a non-aromatic group that includes straight and branched chain aliphatic as well as alicyclic groups or radicals that contain only carbon and hydrogen. Inasmuch as alicyclic groups are cyclic aliphatic groups, such substituents are deemed hereinafter to be subsumed within the aliphatic groups. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups, substituents, moieties or radicals, as discussed hereinafter. An aralkyl substituent group such as benzyl is deemed an aromatic group. A substituent group containing both an aliphatic ring and an aromatic ring portion such as tetralin (tetrahydronaphthalene) that is linked directly through the aliphatic portion to the X group is deemed a non-aromatic, hydrocarbyl group. On the other hand, a similar group bonded directly to the X group via the aromatic portion, is deemed to be a substituted aromatic group. Where a specific aliphatic hydrocarbyl substituent group is intended, that group is recited; i.e., $C_1$-$C_4$ alkyl, methyl or dodecenyl. Exemplary hydrocarbyl groups contain a chain of 1 to about 12 carbon atoms, and preferably 1 to about 8 carbon atoms, and more preferably 1 to 4 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, isoamyl, hexyl, octyl, decyl, dodecyl and the like. Cyclic alkyl radicals such as cyclopropyl, cyclobutyl, cyclopentyl, cyclohexyl and cycloheptyl are also contemplated, as are their corresponding alkenyl and alkynyl radicals. Examples of suitable straight and branched chain alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of straight and branched chain alkynyl radicals include ethynyl, 2-propynyl, 3-propynyl, decynyl, 1-butynyl, 2-butynyl, 3-butynyl, and the like.

As a skilled worker will understand, a substituent that cannot exist such as a $C_1$ alkenyl or alkynyl group is not intended to be encompassed by the word "hydrocarbyl", although such substituents with two or more carbon atoms are intended.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature.

Illustrative hydrocarbyloxy groups include methoxy, ethoxy, and cyclohexenyloxy groups. On the other hand, a hydrocarbyl group containing a —C(O)— functionality is referred to as a hydrocarboyl (acyl) and that containing a —C(O)O— is a hydrocarboyloxy group inasmuch as there is no ambiguity. Exemplary hydrocarboyl and hydrocarboyloxy groups include acyl and acyloxy groups, respectively, such as acetyl and acetoxy, acryloyl and acryloyloxy.

Amide, ester and thioester links can be formed between an alicyclic, aromatic or heteroaromatic ring containing a C(O) group and a nitrogen, oxygen or sulfur atom, respectively. Similarly, a guanidino linker can be formed between an alicyclic, aromatic or heteroaromatic ring containing a NHC(NH) group and a nitrogen, a urethane, carbonate or thiocarbonate can be formed between an aromatic or heteroaromatic ring containing a OC(O) group and a nitrogen, oxygen or sulfur, respectively. A compound containing a urea linker, urethane linker or isothiourea linker [NHC(O)S] can be formed between an alicyclic, aromatic or heteroaromatic ring containing a NHC(O) group and a nitrogen, oxygen or sulfur, respectively.

A "carboxyl" substituent is a —C(O)O H group. A $C_1$-$C_6$ hydrocarbyl carboxylate is a $C_1$-$C_6$ hydrocarbyl ester of a carboxyl group. A carboxamide is a —C(O)$NR^3R^4$ substituent, where the R groups are defined elsewhere. Similarly, a sulfonamide is a —$S(O)_2NR^3R^4$ substituent, where the R groups are defined hereinafter. Illustrative $R^3$ and $R^4$ groups that together with the depicted nitrogen of a carboxamide form a 5-7-membered ring that optionally contains 1 or 2 additional hetero atoms that independently are nitrogen, oxygen or sulfur, include morpholinyl, piperazinyl, oxathiazolyl, 1,2,3-triazolyl, 1,2,4-triazolyl, pyrazolyl, 1,2,4-oxadiazinyl and azepinyl groups.

The term "aryl", alone or in combination, means a phenyl, naphthyl or other radical as recited hereinafter that optionally carries one or more substituents selected from hydrocarbyl, hydrocarbyloxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, and the like. The term "arylhydrocarbyl", alone or in combination, means a hydrocarbyl radical as defined above in which one hydrogen atom is replaced by an aryl radical as defined above, such as benzyl, 2-phenylethyl and the like.

The term "arylhydrocarbyloxycarbonyl", alone or in combination, means a radical of the formula —C(O)—O-arylhydrocarbyl in which the term "arylhydrocarbyl" has the significance given above. An example of an arylhydrocarbyloxycarbonyl radical is benzyloxycarbonyl.

The term "aryloxy" means a radical of the formula aryl-O— in which the term aryl has the significance given above. The term "aromatic ring" in combinations such as substituted-aromatic ring sulfonamide, substituted-aromatic ring sulfinamide or substituted-aromatic ring sulfenamide means aryl or heteroaryl as defined above.

DETAILED DESCRIPTION OF THE INVENTION

The present invention contemplates a compound, a composition containing an anti-bacterial amount of the compound and an antibacterial method of using the compound alone or in conjunction with a synergistic amount of a) a human cathelicidin antimicrobial peptide LL-37 or b) an antibiotic that targets the cell wall and/or the cell membrane.

Compounds

The present invention contemplates a compound corresponding in structure to structural Formula I or a pharmaceutically acceptable salt of that compound

I

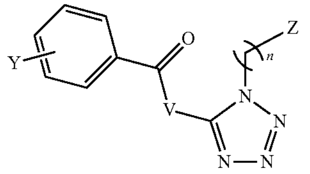

wherein V is O or $NR^9$, Y is halogen, $OR^{10}$, $C_1$-$C_4$ hydrocarbyl or $NHR^{10}$, Z is $NR^2$—X—$R^1$ or $CH_2$—$R^8$, and n is 1-6. In a compound of Formula I, X is hydrido (H), $S(O)_2$, C(O), C(O)$NR^7$, C(NH)$NR^7$ or C(O)O, with the proviso that when X is H, $R^1$ and $CH_2$—$R^8$ are absent. Preferably, X is other than H, and is $S(O)_2$ or C(O). $R^9$ is hydrido (H) or $C_1$-$C_4$ hydrocarbyl; and $R^{10}$ is hydrido or $C_1$-$C_4$ hydrocarbyl. $R^1$ and $R^8$ are the same or different, and each can be an alicyclic, aromatic or heteroaromatic ring system containing one ring or two fused rings each having 5-7 atoms in the ring. A heterocyclic ring system can contain one, two, three or four ring atoms that are other than carbon. Such non-carbon ring atoms are nitrogen, sulfur and oxygen [N, S and O].

The ring system can contain up to three substituents ($R^{1a}$, $R^{1b}$, and $R^{1c}$) other than hydrogen bonded to the ring atoms that themselves can be the same or different. Each of those three groups, $R^{1-c}$, is separately selected from the group consisting of $C_1$-$C_6$ hydrocarbyl, $C_1$-$C_6$ hydrocarbyloxy, $C_1$-$C_6$ hydrocarbyloxycarbonyl, trifluoromethyl (—$CF_3$), trifluoromethoxy (—$OCF_3$), $C_1$-$C_7$ hydrocarboyl (acyl), hydroxy-, halogen, halogen-substituted $C_1$-$C_7$ hydrocarboyl, $C_1$-$C_6$ hydrocarbylsulfonyl, $C_1$-$C_6$ hydrocarbyloxysulfonyl, nitro, phenyl, benzyl, cyano, carboxyl, $C_1$-$C_7$ hydrocarbyl carboxylate [C(O)O—$C_1$-$C_7$ hydrocarbyl], carboxamide [C(O)$NR^3R^4$] or sulfonamide [$S(O)_2NR^3R^4$] wherein the amido nitrogen in either the carboxamide or sulfonamide group has the formula $NR^3R^4$ in which $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N═N— and Ar is a single-ringed aryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur. $R^2$ and $R^7$ are the same or different and are hydrido (H) or $C_1$-$C_4$ hydrocarbyl. In preferred practice, n is 2-4, and more preferably 2.

A particularly preferred compound corresponds in structure to Formula II, below, or a

II

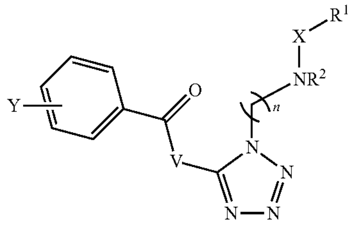

pharmaceutically acceptable salt of that compound in which V, X, Y, n, $R^1$ and $R^2$ are as defined above.

In structural Formula II, X is preferably $S(O)_2$, C(O), C(O)$NR^7$, C(NH)$NR^7$ or C(O)O. V is preferably NH, and Y is preferably halogen, and more preferably chloro or fluoro. $R^1$ is an alicyclic, aromatic or heteroaromatic ring system containing one ring or two fused rings each having 5-7 atoms in the ring. A heterocyclic ring system can contain one, two, three or four ring atoms that are other than carbon. Such non-carbon ring atoms are nitrogen, sulfur and oxygen [N, S and O].

The $R^1$ ring system can contain up to three substituents ($R^{1a}$, $R^{1b}$, and $R^{1c}$) other than hydrogen bonded to the ring atoms that themselves can be the same or different. Each of those three groups, $R^{1a-c}$, is separately selected from the group consisting of $C_1$-$C_6$ hydrocarbyl, $C_1$-$C_6$ hydrocarbyloxy, $C_1$-$C_6$ hydrocarbyloxycarbonyl, trifluoromethyl (—$CF_3$), trifluoromethoxy (—$OCF_3$), $C_1$-$C_7$ hydrocarboyl (acyl), hydroxy-, halogen, halogen-substituted $C_1$-$C_7$ hydrocarboyl, $C_1$-$C_6$ hydrocarbylsulfonyl, $C_1$-$C_6$ hydrocarbyloxysulfonyl, nitro, phenyl, benzyl, cyano, carboxyl, $C_1$-$C_7$ hydrocarbyl carboxylate [C(O)O—$C_1$-$C_7$ hydrocarbyl], carboxamide [C(O)$NR^3R^4$] or sulfonamide [$S(O)_2NR^3R^4$] wherein the amido nitrogen in either the carboxamide or sulfonamide group has the formula $NR^3R^4$ in which $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N═N— and Ar is a single-ringed aryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur. $R^2$ and $R^7$ are the same or different and are hydrido (H) or $C_1$-$C_4$ hydrocarbyl.

In some preferred embodiments of compounds of one or both of Formulas I and II, X is $S(O)_2$, whereas in other preferred embodiments, X is C(O). Thus, in a first such preferred embodiment, a compound is a sulfonamide, whereas in a second preferred embodiment, the compound is a carboxamide.

It is separately preferred that the $R^1$ (and also $R^8$) group be a relatively large group so that $R^1$ (and $R^8$) is preferably a two fused ring system rather than a single ring. Illustrative two fused ring systems include naphthyl, benzofuranyl, isobenzofuranyl, indoyl, pyrano[3,4-b]pyrrolyl, benzoxazolyl, anthranil, tetralinyl, decalinyl, benzopyryranyl, quinolinyl, isoquinolinyl, cinolinyl, quinazolinyl, pyrido[3,2-b]pyridinyl, purinyl, 1,4,2-benzoxazinyl, thionaphthenyl, isothionaphtheneyl, benzimidazolyl, benzimidazolinyl, benzthiazolyl, benzoxazolyl and the like. It is further preferred that the ring bonded directly to X itself be aromatic, whereas the ring to which the aromatic ring is fused need not itself also be aromatic, although preferably both rings are aromatic.

It is additionally preferred that the $R^1$ group contain at least one substituent. One preferred substituent is a $NR^5R^6$ group, where $R^5$ and $R^6$ are both $C_1$-$C_4$ hydrocarbyl, such as methyl ($C_1$) or $R^5$ and $R^6$ together with the depicted nitrogen form a 5-7-membered ring that contains 1 or 2 additional hetero atoms that independently are nitrogen, oxygen or sulfur, such as a N-morpholinyl group.

$R^2$ and $R^7$ are both preferably hydrido (H).

Illustrative preferred compounds are shown below in Formulas III and IIIB-IIIG.

III

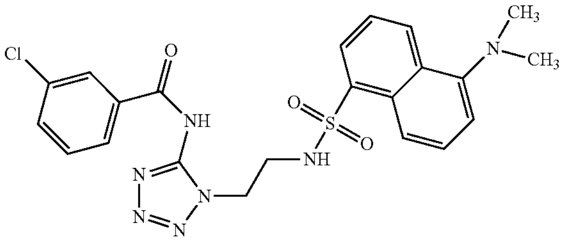

IIIA

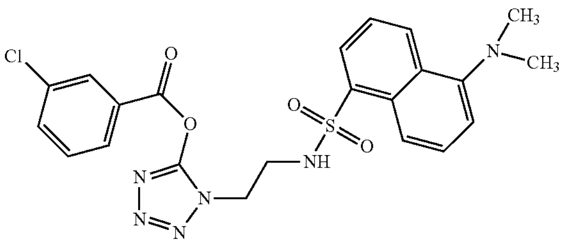

IIIB

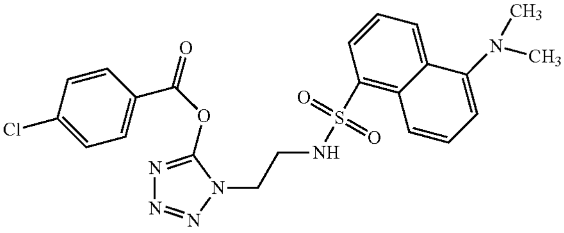

IIIC

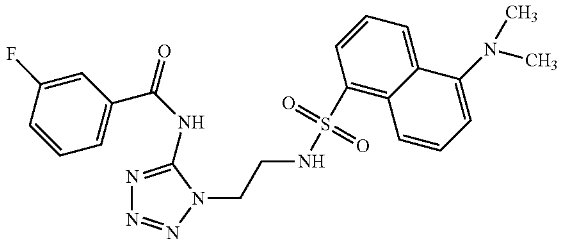

-continued

IIID

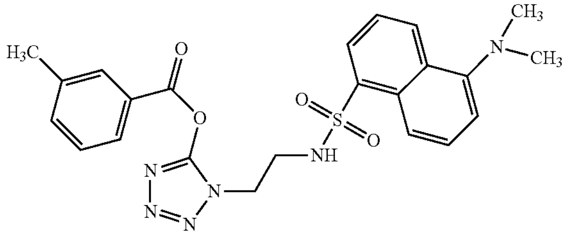

IIIE

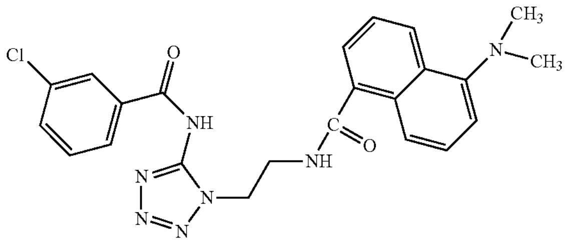

IIIF

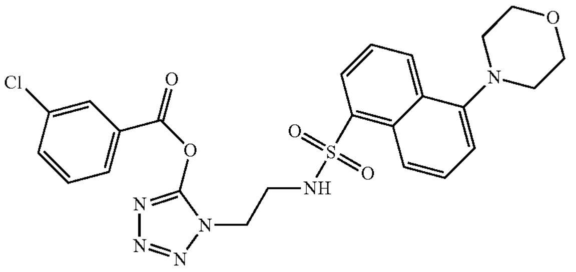

IIIG

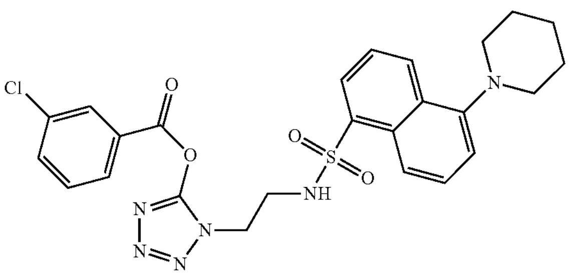

Methods and Pharmaceutical Compositions

A contemplated compound useful in a method of the invention can be provided for use by itself, or as a pharmaceutically acceptable salt. Regardless of whether in the form of a salt or not, a contemplated composition is typically dissolved or dispersed in a pharmaceutically acceptable diluent or carrier that forms a pharmaceutical composition and that pharmaceutical composition is administered to the cells in culture or to the cells of a host mammal.

A contemplated pharmaceutical composition contains an amount of a contemplated compound or a pharmaceutically acceptable salt thereof dissolved or dispersed in a physiologically tolerable diluent or carrier that is effective to provide a bacteriostatic or bactericidal treatment (an antibacterial effective amount) for bacteria. Bacteria contemplated for such treatment particularly include Gram positive bacteria such as *B. anthracis, B. subtilis, Streptococcus mutans, M. tuberculosis* and *S. aureus*, including the methicillin-susceptible strain, Newman, and the MRSA strain, Sanger 252, and also for Gram negative bacteria such as *E. coli* or *Shigella*

*flexneri* having impaired drug efflux systems or when administered along with a) the human cathelicidin antimicrobial peptide LL-37 or b) an antibiotic that targets the cell wall and/or the cell membrane. The bacteria can be treated when present in a cell culture or as an infection in a mammal.

A contemplated pharmaceutical composition can be contacted with (administered or provided to) bacteria or bacterially-infected mammalian cells in vitro as in a cell culture, or in vivo as in an infected, living, host mammal in need.

A contemplated composition is typically administered a plurality of times over a period of days to thereby contact the cells to be treated. More usually, a contemplated composition is administered once or twice daily. It is contemplated that once administration of a contemplated compound has begun, the compound will be administered chronically for the duration of the study being carried out or until the desired bacterium has been eliminated or its growth slowed or stopped sufficiently so that a treated mammal's immune system can eliminate the infection.

A contemplated compound is usually utilized at picomolar to micromolar to millimolar amounts. Thus, an effective amount of a contemplated compound present in a contemplated pharmaceutical composition is that which provides a concentration of about 100 picomolar to about 1000 micromolar (1 millimolar) to a host animal's blood stream or to an in vitro cell medium in practicing a contemplated method of the invention. A more usual amount is about one micromolar to about 500 micromolar. A skilled worker can readily determine an appropriate dosage level of a contemplated compound to inhibit a desired amount of fucosylation and/or sialylation.

A further aspect of the invention contemplates a method of inhibiting the growth of bacteria, and particularly Gram positive bacteria, that comprises the steps of contacting the bacteria with an antibacterial amount of a compound of Formula I or its pharmaceutically acceptable salt. In one aspect, the bacterium is *B. anthracis*, whereas in another aspect, the bacterium is *S. aureus*, including the Newman and Sanger 252 strains; both being Gram positive bacteria. In further aspects, the bacteria can be *M. tuberculosis, B. subtilis* or *Streptococcus mutans*, which are also Gram positive bacteria.

Gram negative mutants whose drug efflux systems have been impaired as by compounds such as L-phenylalanyl-L-arginyl beta-naphthylamide dihydrochloride (MC-207110), D-Orn-DhPhe-aminoquinoline (MC-02595), and 4-aminomethyl-2-pyrrolindinecarboxamide-D-hPhe-6-aminoquinoline (MC-04124), or whose ClpXp protease system is impaired as by a compound discussed in inhibition such as *E. coli, Shigella flexneri* or *Caulobacter crescentus* in Cheng et al., *Protein Sci.* 2007 16:1535-1542.

The contacted bacteria can be present in a cell culture or in an infected mammal. When the latter is the case, the bacteria are contacted by administration of a compound of Formula I to the infected mammal. Particularly when the treated bacteria are present in an infected mammal, the bacteria are contacted a plurality of times.

In case of any antibacterial method discussed herein, the compound of Formula I or its pharmaceutically acceptable salt is preferably present in a pharmaceutical composition as discussed above. A particularly preferred compound of Formula I such as a compound of Formula III is often referred to herein as Dansyl-F2 and has the structural formula

III

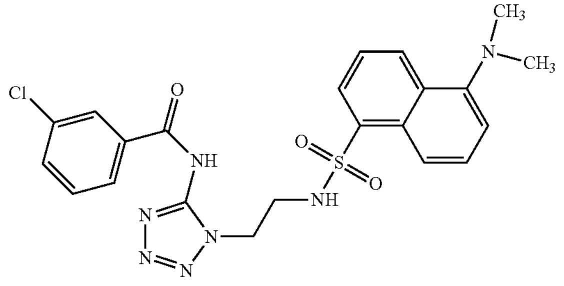

Another aspect of the invention contemplates the use of a contemplated compound to provide enhanced inhibition of the microbial ClpXP protease enzyme, thereby providing enhanced synergistic antimicrobial activity with cathelicidin antimicrobial peptides and antibiotics that target the cell and/or cell membrane such as penicillin and daptomycin in Gram positive bacteria such as *B. anthracis* and drug resistant strains of *S. aureus*. The ClpXP inhibition provided by a contemplated compound is typically enhanced relative to that provided by F2 by a factor of about 2 to about 5. Like F2, a contemplated compound can simultaneously sensitize pathogenic bacteria to host defenses and pharmaceutical antibiotics.

Thus, use of both 1) a contemplated compound and 2) a) the human cathelicidin antimicrobial peptide LL-37 or b) an antibiotic that targets the cell wall and/or the cell membrane can kill treated Gram positive bacteria at concentrations of the two active components that are separately ineffective by themselves to kill the bacteria. A similar synergistic effect can be obtained with Gram negative bacteria when a drug efflux system-impairing drug such as the before-mentioned L-phenylalanyl-L-arginyl beta-naphthylamide dihydrochloride (MC-207110), D-Orn-D-hPhe-aminoquinoline (MC-02595), and 4-aminomethyl-2-pyrrolindinecarboxamide-D-hPhe-6-aminoquinoline (MC-04124). Illustrative cell wall-targeting antibacterials include the beta-lactam antibacterials like a penicillin (e.g. ampicillin), a cephalosporin and a monobactam. Daptomycin is an illustrative cell membrane targeting antibacterial agent.

In this instance, the concentration of a contemplated compound is about one-half or less that of F2 that accomplishes the same result. Illustrative concentrations are about one-half the MIC value determined for in vitro cultured bacteria to be killed or whose growth is to be inhibited. Because the two components work together, the amount of each utilized is referred to a synergistic amount.

Thus, another contemplated method of inhibiting the growth of bacteria that comprises the steps of contacting the bacteria with a synergistic amount of a compound or its pharmaceutically acceptable salt of Formula I and a synergistic amount of a) a human cathelicidin antimicrobial peptide LL-37 or b) an antibiotic that targets the cell wall and/or the cell membrane for Gram positive bacteria, and the same for Gram negative bacteria plus the addition of an effective amount of an efflux system-impairing drug, as noted above.

A contemplated pharmaceutical composition can be administered orally (perorally), parenterally, by inhalation spray in a formulation containing conventional nontoxic pharmaceutically acceptable carriers, adjuvants, and vehicles as desired. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

For injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline. Liquid pharmaceutical compositions include, for example, solutions suitable for parenteral administration. Sterile water solutions of an active component or sterile solution of the active component in solvents comprising water, ethanol, or propylene glycol are examples of liquid compositions suitable for parenteral administration.

In addition, sterile, fixed oils are conventionally employed as a solvent or suspending medium. For this purpose any bland fixed oil can be employed including synthetic mono- or diglycerides.

In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Sterile solutions can be prepared by dissolving a contemplated compound in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. In such solid dosage forms, a contemplated compound is ordinarily combined with one or more excipients appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets, capsules and pills can additionally be prepared with enteric coatings, and such coatings are preferred.

A mammal in need of treatment and to which a pharmaceutical composition containing a contemplated compound is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like. Where in vitro mammalian cell contact is contemplated, a culture of cells from an illustrative mammal is often utilized, as is illustrated hereinafter.

Preferably, the pharmaceutical composition is in unit dosage form. In such form, the composition is divided into unit doses containing appropriate quantities of the active agent. The unit dosage form can be a packaged preparation, the package containing discrete quantities of the preparation, for example, in vials or ampules.

A compound of the invention can be provided for use by itself, or as a pharmaceutically acceptable salt. A contemplated compound is an amine and can typically be used in the form of a pharmaceutically acceptable acid addition salt derived from an inorganic or organic acid. Exemplary salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

The reader is directed to Berge, *J. Pharm. Sci.* 68(1):1-19 (1977) for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the salt prepared need not be pharmaceutically acceptable.

Compound Synthesis

A contemplated compound is readily prepared using chemistry that should be readily understood by a skilled worker. An illustrative synthesis of the intermediate, N-(1-(2-aminoethyl)-1H-tetrazol-5-yl)-3-chlorobenzamide, and the preferred dansyl derivative are set out hereinafter in Scheme 1. Specific syntheses of several of the compounds prepared and assayed herein are also set out hereinafter along with physical data for the new compounds. A more general synthesis for additional contemplated compounds is illustrated below in Scheme 2.

As will be seen in Scheme 2, sulfonamide linkages are readily formed by reaction of the amine of N-(1-(2-aminoethyl)-1H-tetrazol-5-yl)-3-chlorobenzamide with a sulfonyl halide such as Compound A in methylene chloride as solvent in the presence of a base. A carboxamide can similarly be formed by reaction of an acyl halide such as Compound B with the same starting material. Using that same omega-amine starting material and reacting it with an isocyanate-containing compound such as Compound C forms a urea linkage, whereas reaction with a halocarbonate-containing compound such in Compound D forms a urethane linkage.

Scheme 2
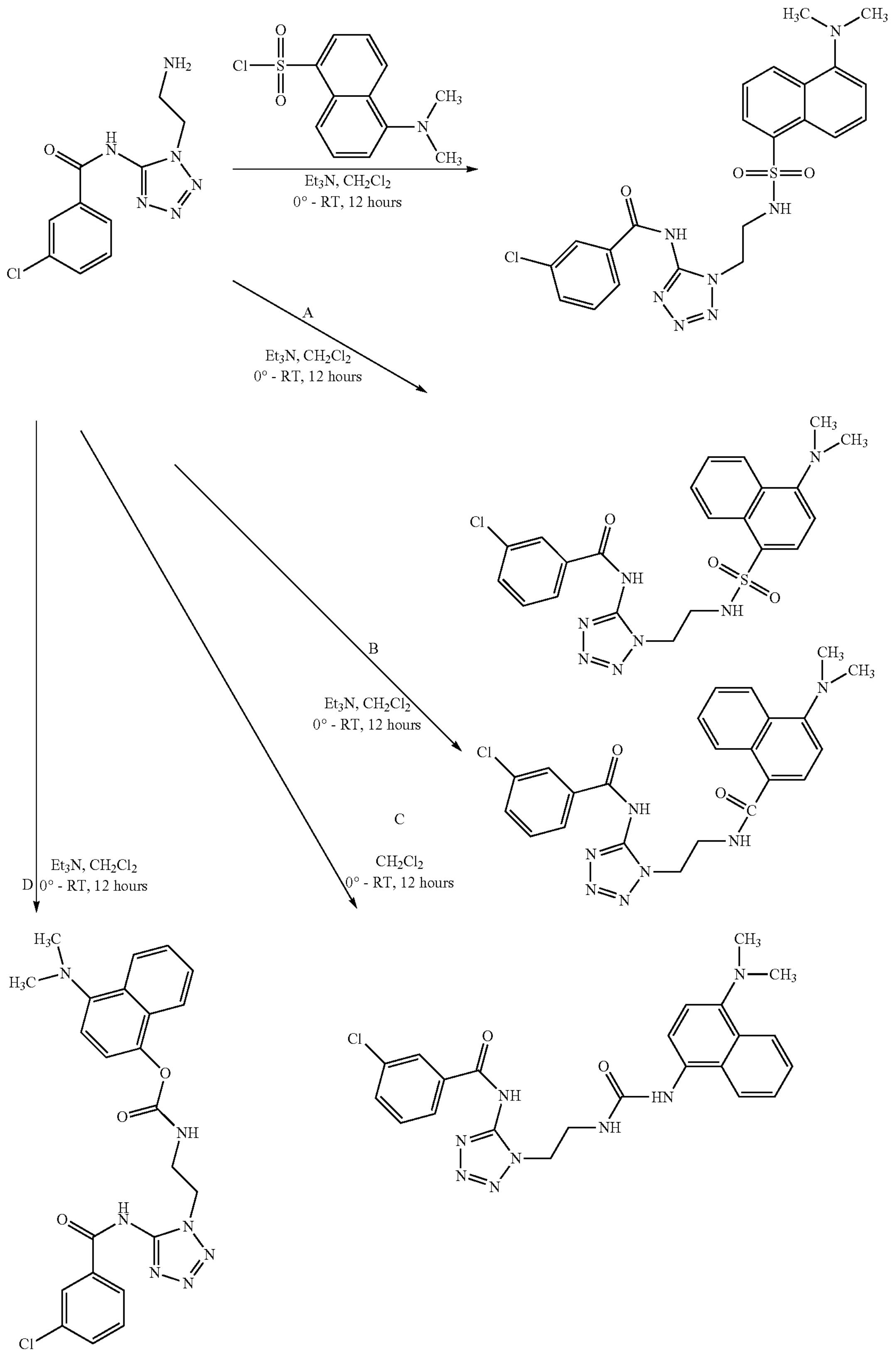

-continued

A = 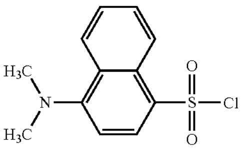 B = 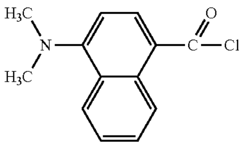 C = 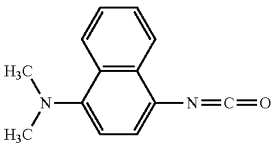 D = 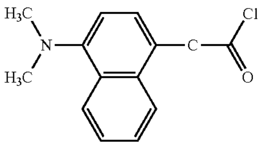

A general synthetic scheme for ester preparation is shown below as Scheme 3, wherein the steps of Scheme 2, above are followed for the later steps, and in which Y, n, $R^1$ and $R^2$ are as described for Formula I.

Scheme 3

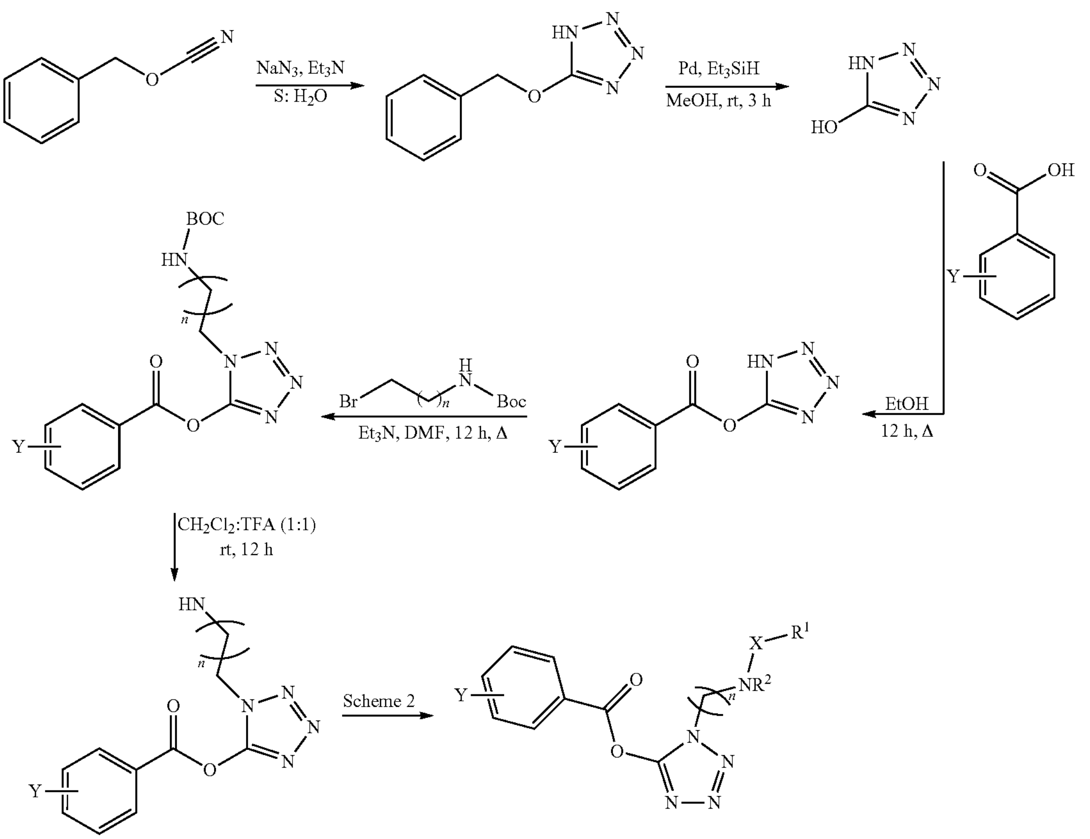

Bactericidal/Bacteristatic Assays

Protocol

Overnight (about 18 hours) cultures of *B. anthracis* Sterne ($pXO1^+$, $pXo2^-$), *B. subtilis* and *S. flexneri* were grown in plain LB medium. The following morning cultures were inoculated into a flask containing 25 ml of fresh LB at a starting $OD_{600}$ 0.002. Cultures were then transferred into pre-designated wells in 96 well plates such that lane A contained 95 μl of culture, whereas the rest of the plate contained 50 μl of culture per well (separate plates were used to analyze the different strains).

Five microliters (5 μl) of the highest drug concentrations were added to the top lane in triplicate from DMSO stocks. The assay plates included untreated as well as DMSO controls. Drugs were then serially diluted (2 fold dilutions) and the plates were sealed with a thermal seal membrane to prevent evaporation. Plates were incubated at 37° C. for 24 hours. Plates were spun down using a Beckmann S2096 plate rotor on an Allegra® X-22R centrifuge. Growth in plates was then inspected visually and the minimal inhibitory concentration (MIC) determined as the lowest inhibitor concentration that inhibited visible growth. The results of this assay are shown below in Table 1.

TABLE 1

| | MIC (μM) | | |
|---|---|---|---|
| Strain ID | F2 | Dansyl-F2 | CPD D* |
| *B. anthracis* | 31.2 | 7.8 | >200 |
| *B. subtilis* | 26.1 | 13.3 | >200 |
| *S. flexneri* | 7.8 | >200 | >200 |

*See, Compound D, below, after Table 3.

Half Maximal Growth Inhibitory Concentration ($IC_{50}$) Determination

Protocol

Overnight (about 18 hours) cultures of *B. anthracis* Sterne ($pXO1^+$, $pXO2^-$; WT), *B. anthracis* ΔclpX, *B. anthracis* ΔclpX+pclpX, WT+pUTE29 (empty vector), ΔclpX+pUTE29 and *S. flexneri* (a Gram negative bacterium) were grown in plain LB medium. The following morning cultures were inoculated into a flask containing 20 ml of fresh LB at a starting $OD_{600}$ 0.002. Cultures were then transferred into pre-designated wells in 96 well microplates and drugs were titrated at concentrations determined based on the MIC with each concentration being analyzed in triplicate to a final volume of 100 μl (separate plates were used to analyze the different strains).

Similarly, the each assay plate included untreated as well as DMSO controls. Plates were incubated at 37° C. for 24 hours. Cultures were then diluted 2-fold with fresh medium and transferred to sterile clear flat bottomed 96 well microplates for $OD_{600}$ readings. $OD_{600}$ was recorded on a SpectraMax® M2 microplate reader (Molecular Devices). Inhibition was analyzed as growth in the presence of an inhibitor relative to untreated controls as illustrated in FIG. 1. The results of this assay are shown in Table 2 below.

TABLE 2

| | $IC_{50}$ (μM) | |
|---|---|---|
| Strain ID | F2 | Dansyl-F2 |
| WT *B. anthracis* | 17.6 | 5.28 |
| ΔclpX | 27.0 | 5.93 |
| ΔclpX + pclpX | 14.8 | 6.22 |
| WT + pUTE29 | 27.5 | 9.88 |
| ΔclpX + pUTE29 | 22.3 | 6.28 |
| *S. flexneri* | 5.95 | >200 |

Using similar procedures several further F2 derivative compounds were assayed for potential bactericidal/bacteriostatic activity against *B. anthracis* Sterne ($pXO1^+$, $pXO2^-$) and *S. flexneri*. The results of those assays are shown in Table 3, below. The structures of numbered derivatives are shown hereinafter, with their compound number in parentheses.

TABLE 3

| Compound # | MIC[1] *S. flexneri* (μM) | MIC[1] *B. anthracis* (μM) |
|---|---|---|
| F2 | 3.13 | 25.0 |
| 1 | >500 | >500 |
| 2 | 250 | >500 |
| 3 | >500 | >500 |
| 4 | >500 | >500 |
| 5 | >500 | >500 |
| 6 | >500 | >500 |
| 7 | >500 | >500 |
| 8 | >500 | >500 |
| 9 | >500 | >500 |
| 10 | >500 | >500 |
| 11 | 500 | >500 |
| 12 | >500 | >500 |
| 13 | >500 | >500 |

[1]MIC values were identical in two separate determinations.

Further assays were carried out to determine MIC values using Compounds F2, Dansyl-F2, A, D and E that are shown in Scheme 1, below, along with Compounds 14, 15, and 16 whose structures are illustrated hereinafter.

F2

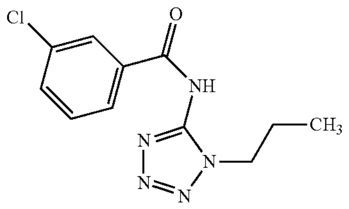

A

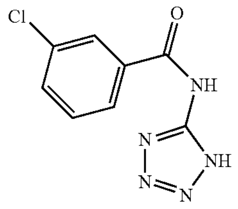

D

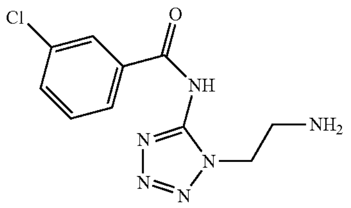

14

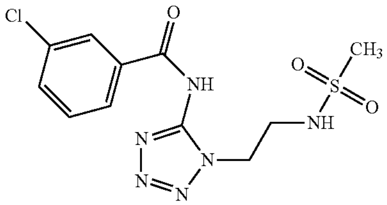

15

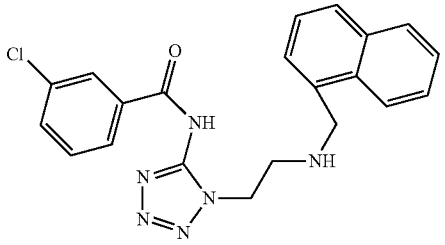

16

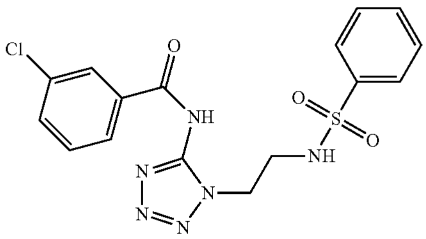

-continued (E)

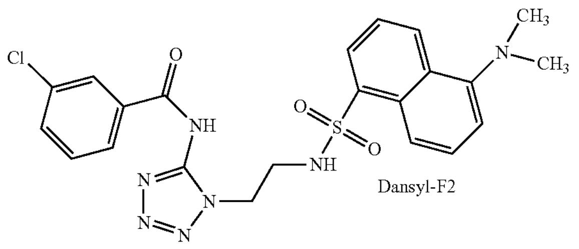

Dansyl-F2

These assays were carried out as described for the MIC assays of Table 1. *Mycobacterium smegmatis* is useful for the research analysis of other *Mycobacteria* species in laboratory studies. *M. smegmatis* is commonly used in work on the mycobacterium species due to its being a "fast grower" and non-pathogenic, requiring only a biosafety level 1 laboratory. This species shares more than 2000 homologs with *M. tuberculosis* and shares the same unusual cell wall structure of *M. tuberculosis* and other mycobacterial species. *M. smegmatis* is therefore a frequently used model for mycobacterial species. *M. smegmatis* is a Gram positive bacterium. The data from this study are shown below in Table 4.

TABLE 4

| | MIC (μM) | | |
|---|---|---|---|
| Compound | *Shigella flexneri* | *Bacillus anthracis* | *Mycobacterium smegmatis* |
| F2 | 3.1 | 25 | 25 |
| Dansyl-F2 (E) | NA | 5.3 | NA |
| A | NA | NA | NA |
| D | NA | NA | — |
| 14 | NA | NA | — |
| 15 | NA | NA | — |
| 16 | NA | 400 | — |

A similar MIC study to those discussed above was carried out with TolC mutants of the Gram negative bacteria *E. coli* and *S. flexneri*. TolC is an outer membrane protein that has been implicated in many diverse cellular functions, including toxin secretion. [Vakharia et al., *J Bacteriol* 183(23):6908-6916 (2001).] TolC is involved in the secretion of alpha-hemolysin secretion and the TolC mutant studied are defective in secretion of alpha-hemolysin. The data from that study are shown below in Table 5.

TABLE 5

| | MIC (μM) | |
|---|---|---|
| Compound | *E. coil* TolC | *S. flexneri* TolC |
| F2 | 12.5 | 3.12 |
| Dansyl-F2 (E) | 25 | 6.25 |

Inhibition of Spore Germination

Spore germination in *B. anthracis*, a Gram positive organism, is a key step to its pathogenesis following infection. Inhibition of this transformation into vegetative bacteria can be considered as a prophylactic form of treatment that could prevent the onset of the disease. Consequently, novel inhibitors of spore germination provide a glimmer of hope towards tackling this deadly disease. Such inhibitors could be used directly to prevent fatality or in combination therapy.

It has been found that F2 and Dansyl-F2 inhibit *B. anthracis* spore germination in vitro under physiologic conditions. Thus, cultures of aliquots from spores that germinated into vegetative cells in the absence of F2 or dansyl-F2 were treated with 50 μM F2 or 50 μM dansyl-F2 and assayed 20 hours after initiation. No vegetative cells were observed in either the F2- or dansyl-F2-treated cultures.

Inhibition of Trans-Translation In Vitro

In vitro trans-translation assays were performed on *E. coli* extracts using the PURExpress (New England Biolabs) protein synthesis kit with a DHFR template lacking the stop codon and [$^{35}$S]-methionine, according to the manufacturer's instructions, with the addition of 2 μM tmRNA and SmpB. Inhibitor compounds were added to 10 μM final concentration. Tagging efficiency was calculated as the ratio of tagged DHFR to total DHFR (tagged+untagged) from at least 3 repeats. The % inhibition was calculated using the control reaction with no inhibitor as 100%. No inhibition was observed when a DHFR template containing a stop codon was used, indicating that the inhibitors specifically affect trans-translation and not translation. The results are shown below in Table 6.

TABLE 6

| Compound ID | % inhibition in vitro |
|---|---|
| F2 | 88.0 |
| 4 | 74.9 |
| 10 | 68.1 |
| 11 | 57.9 |
| 12 | 44.6 |
| 13 | 71.6 |
| 9 (A) | 78.9 |
| D | 52.3 |
| 14 | 47.8 |
| 16 | 37.0 |
| III (E) | 89.1 |

F2 and Dansyl-F2 Inhibit Growth of *M. tuberculosis*

Auto-luminescent *M. tuberculosis* (LuxTB) was grown to an $OD_{600}$ of 0.0125. The indicated concentrations of F2 and Dansyl-F2 were added to the mycobacterial cultures and luminescence readings were taken every 24 hours using a Tecan Infinite® M200 plate reader. The results are shown in Table 7, below, and indicate an enhanced activity for Dansyl-F2 compared to F2 itself.

TABLE 7

| | $IC_{50}$ (μM) | |
|---|---|---|
| Day | F2 | Dansyl-F2 |
| 2 | 292 | 181 |
| 3 | 226 | 100 |
| 4 | 115 | 96.4 |

Bactericidal Activity of F2 and Dansyl-F2 Against *M. tuberculosis*

Wild-type *M. tuberculosis* was grown to an $OD_{600}$ of 0.0125 and the indicated concentrations of F2 and Dansyl-F2 were added to the mycobacterial cultures. The minimum inhibitory concentration (MIC) of F2 and Dansyl-F2 were determined as the minimum concentration of drug that inhibited visible growth of *M. tuberculosis*. Colony forming units (CFUs) were determined by plating serial dilutions of cultures onto 7H10 agar plates (Difco) supplemented with 10% OADC (Middlebrook) and 0.5% glycerol. Plates were incubated for 3-4 weeks at 37° C. prior to enumeration of CFUs. This study was carried out by Dr. Paolo Manzanillo and Dr. Jeff Cox at the University of California, San Francisco.

Figures 2, 2A:
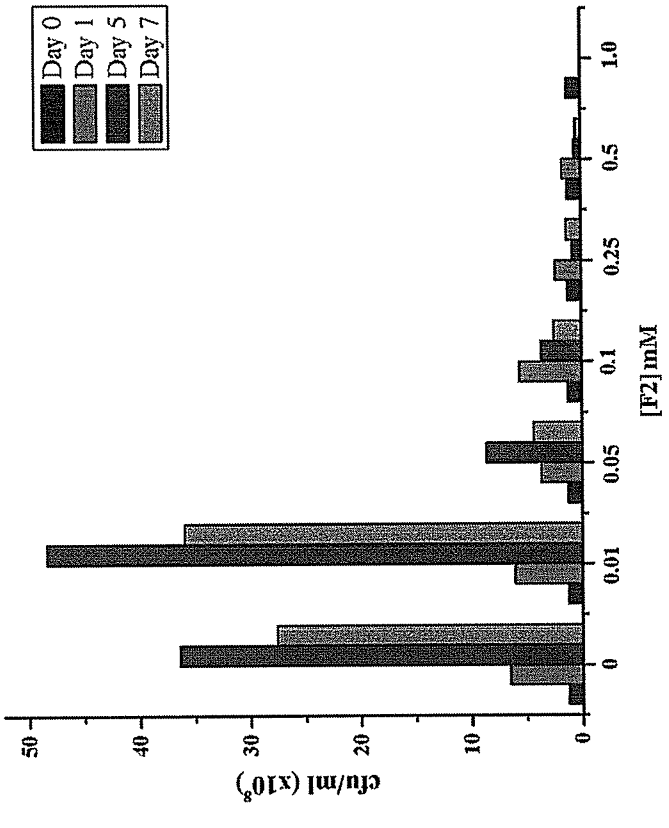
FIG. 2, in two panels as FIG. 2A and FIG. 2B, illustrate a minimum inhibitory concentration (MIC) determination of F2 (FIG. 2A) and Dansyl-F2 (FIG. 2B) for *M. tuberculosis*. It is to be noted that the ordinate extends to $50\times10^8$ cfu/ml for F2 (FIG. 2A), whereas the ordinate for Dansy-F2 extends only to $10\times10^8$ cfu/ml (FIG. 2B).
Figure 2B:
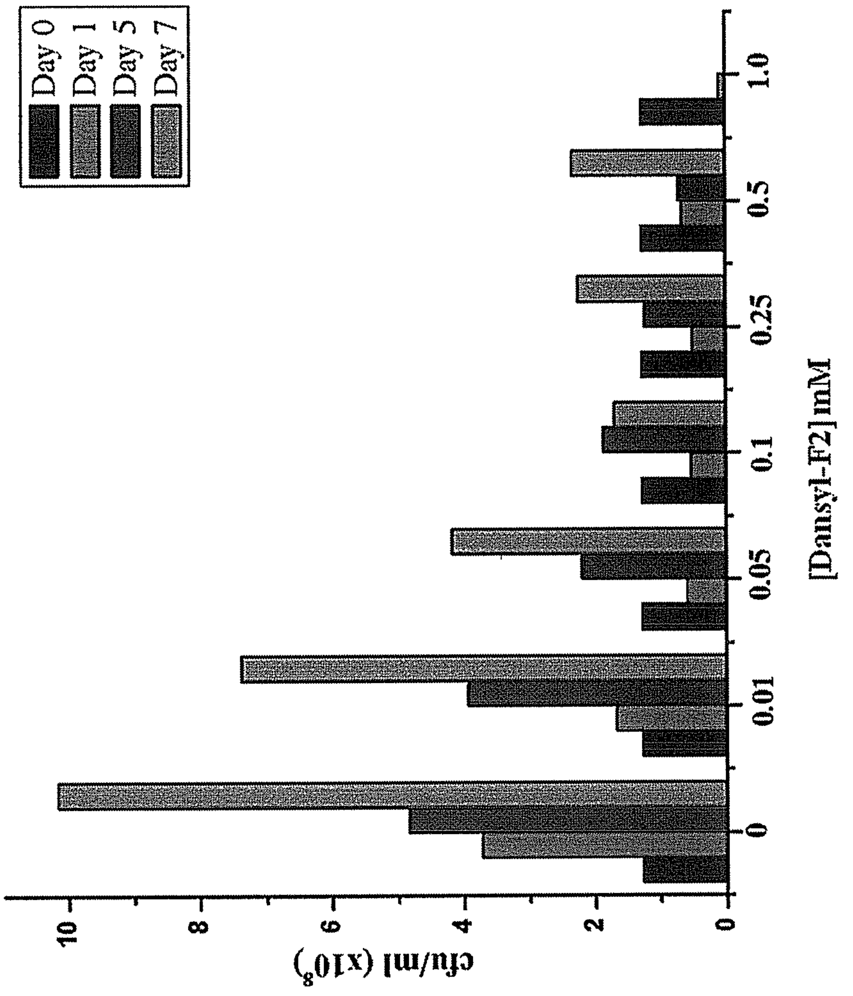

The results of this study are shown in FIG. 2A and FIG. 2B. As will be seen, the results indicate higher activity for Dansyl-F2 than for the parent compound, F2. The MIC for Dansyl-F2 against *M. tuberculosis* was found to be about 50 μM.

Materials

All organic solvents were purchased from VWR International, LLC (Radnor, Pa.) unless otherwise stated. 3-Chlorobenzoic acid, N-(3-dimethyl-aminopropyl)-N'-ethylcarbodiimide (EDC), N-hydroxysuccinimide (NHS), triethylamine (TEA), dichloromethane (DCM), dimethylformamide (DMF), 5-aminotetrazole, biotin, 2-bromo-ethylamine, diisopropylethylamine, Di-tert-butyl dicarbonate, N-hydroxysuccinimide and dimethylsulfoxide-$d_6$ were purchased from Sigma-Aldrich (St. Louis, Mo.). 1-Propyl-1H-tetrazol-5-amine was purchased from ChemBridge Corporation (San Diego, Calif.). Silica gel (60 Å, 60-200 μm) was purchased from VWR International (Bridgeport, N.J.). Thin Layer Chromatography (TLC) silica gel (IB-F) plates were purchased from J. T. Baker (Phillipsburg, N.J.). Chloroform-d was purchased from Cambridge Isotope Laboratories (Andover, Mass.).

Abbreviations

DMF—Dimethylformamide; DIPEA—Diisopropyl-ethylamine; EDC—1-Ethyl-3-(3-dimethylaminopropyl)-carbodiimide; NHS—N-Hydroxysuccinimide; PyBOP—benzotriazol-1-yloxy)tripyrrolidinophosphonium hexafluorophosphate. TFA—Trifluoroacetic acid, DCM—Dichloromethane, Synthesis of F2

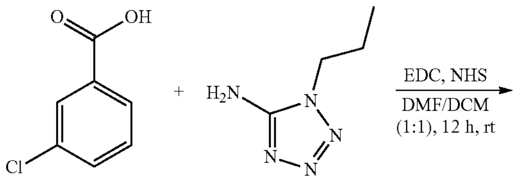

-continued

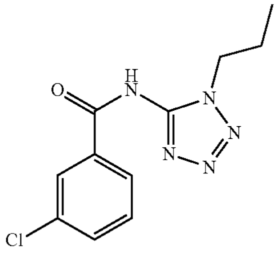

F2

3-Chlorobenzoic acid (250 mg, 1.6 mmol) was added to a bound bottom flask containing a solution of DMF/DCM (1:1) at room temperature. To this mixture was added EDC (297 mg, 1.9 mmol) NHS (221 mg, 1.90 mmol). The reaction was stirred for 5 minutes at room temperature to obtain a uniform solution. A solution of 1-propyl-1H-tetrazol-5-amine (203 mg, 1.6 mmol) in DMF/DCM (1:1) was then added to the flask and the reaction continuously stirred at room temperature while monitoring via TLC. After 12 hours, the reaction was stopped and evaporated to dryness in vacuo.

Ten ml of aq. $NaHCO_3$ (0.5 M) was added to the residual material followed by extraction with DOM (3×20 ml). The product was purified via column chromatography on silica gel and eluted with a $CH_2Cl_2$/MeOH/TEA (9.8:0.1:0.1) solvent system in 65% yield.

$^1$H-NMR (400 MHz, $CDCl_3$): δ0.93 (t, J=7.4, 3H), 1.94 m, 2H), 4.28 (t, J=7.4, 2H), 7.45, (m, 2H), 7.90 (m, 2H), 11.78 (bs, 1H). $^{13}$1C-NMR (100 MHz, $CDCl_3$): δ 10.6, 21.8, 46.7, 124.8, 127.0, 129.7, 131.1, 134.5, 136.6, 161.1, 165.6. MS ESI (+) m/z: calculated for $C_{11}H_{12}ClN_5O$ $[M+H]^+$266.1, observed $[M+H]^+$266.1.

Synthesis of Dansyl-F2

Scheme 1

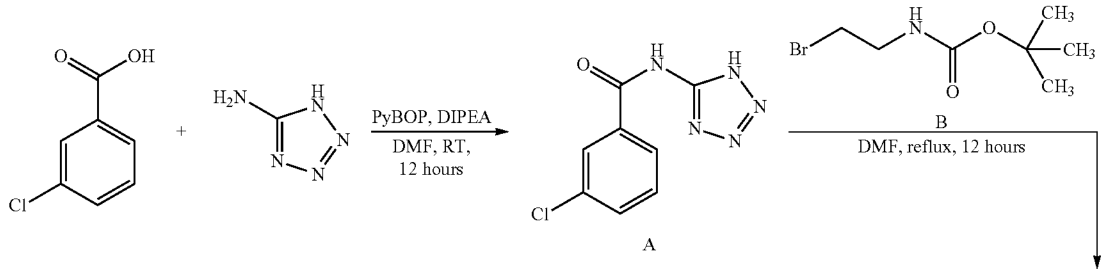

A

B

-continued

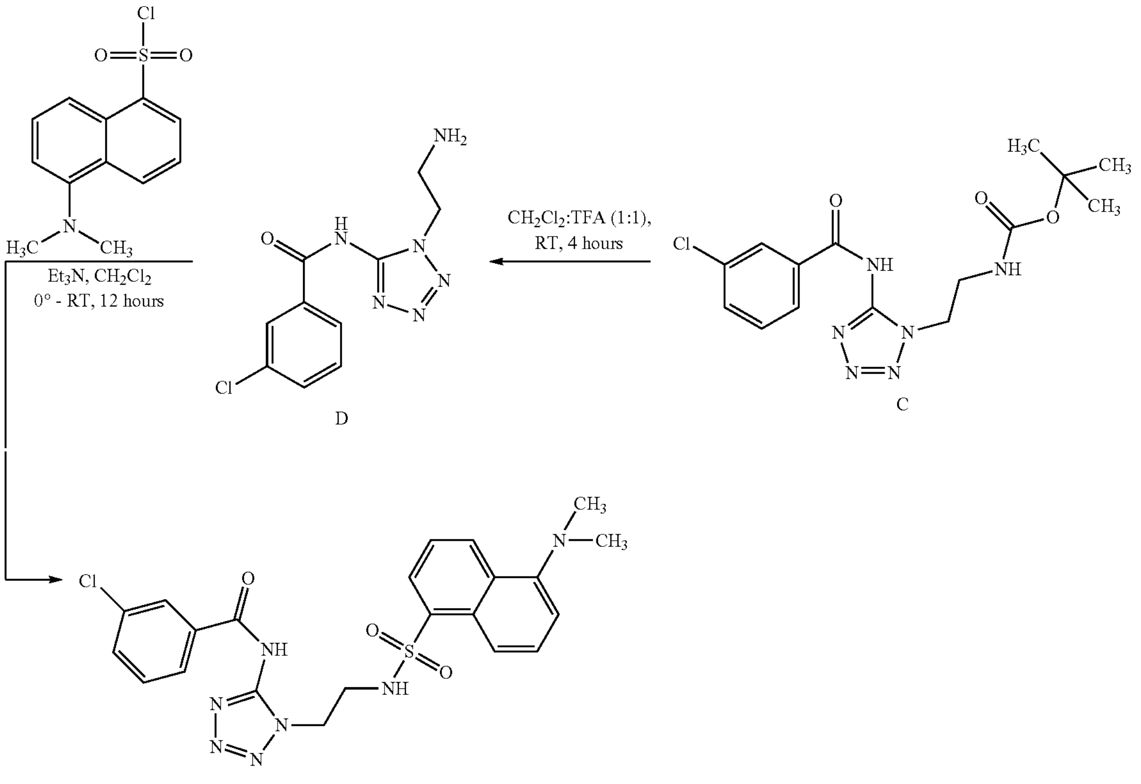

D

C

E
(Dansyl-F2)

3-Chloro-N-(1-propyl-1H-tetrazol-5-yl)benzamide (A)

3-Chlorobenzoic acid (1 g, 6.4 mmol) was added to a bound bottom flask containing 30 ml of DMF at room temperature. DIPEA (4.5 ml, 25.6 mmol) and PyBOP (1.1 g, 7.7 mmol) were then added. The resulting mixture was stirred for an additional 30 minutes at room temperature. A solution of 5-aminotetrazole (1.1 g, 7.7 mmol) in DMF was slowly added to the flask and the reaction stirred continuously for 12 hours. The reaction was terminated and evaporated to dryness in vacuo.

Ten ml of aq. $NaHCO_3$ (0.5 M) was added to the dried sample followed by the addition of 30 ml DCM. The white precipitate that crashed out of solution was isolated by vacuum filtration followed by 3 washes with DCM to give the product, a white powder (67% yield).

$^1$H-NMR (400 MHz, DMSO-d6): δ 6.45 (bs, 1H) 7.60 (t, J=8.0 Hz, 1H), 7.73 (d, J=8.0 Hz, 1H), 8.04 (d, J=6.9 Hz, 1H) 8.14 (s, 1H). $^{13}$C-NMR (100 MHz, DMSO-d6): δ 127.1, 128.2, 130.7, 132.7, 133.5, 133.8, 150.3, 164.3.

tert-butyl-2-bromoethylcarbamate (B)

A solution of 2-bromoethylamine hydrobromide (5 g, 24.4 mmol) in 20 ml $H_2O$ was stirred at room temperature in a round bottom flask. Di-tert-butyl dicarbonate (2.8 g, 12.2 mmol) was dissolved in 40 ml DCM and added to the flask over a period of 10 minutes. To the resulting biphasic mixture was added NaOH (2.0 g, 48.8 mmol) dissolved in 20 ml $H_2O$. This reaction mixture was stirred vigorously at room temperature for 4 hours. The organic layer was then isolated and the aqueous layer extracted once with 20 ml DCM. The combined organic phase was washed once with $H_2O$, then with 0.2 M HCl to a pH of about 1 (monitored using pH paper), and finally with water to a final pH of 6-7 for the aqueous layer. The resulting organic layer was dried over anhydrous $MgSO_4$, filtered and evaporated to dryness in vacuo to give colorless oil in 75% yield. [Beylin et al., OPPI Briefs 1987 19:78-80.]

$^1$H-NMR (400 MHz, $CDCl_3$): δ 1.40 (s, 9H), 3.44 (m, 4H), 5.05 (bs, 1H). $^{13}$C-NMR (100 MHz, $CDCl_3$) δ 28.7, 33.0, 41.0, 80.1, 156.0.

3-Chloro-N-(1-(2-(3,3-dimethylbutanamido)ethyl)-1H-tetrazol-5-yl)benzamide (C)

Compound (A) (250 mg; 1.12 mmol), Compound (B) (250 mg; 1.12 mmol) and 340 mg (3.36 mmol) of $Et_3N$ were added to a round bottomed flask containing 15 ml of DMF and refluxed overnight (about 18 hours). The reaction mixture was evaporated to dryness under reduced pressure and 20 ml of $H_2O$ added. This aqueous phase was extracted with $CH_2Cl_2$ (3×30 ml) and the organic layers combined, dried over $MgSO_4$ and further concentrated. The crude product obtained was purified over silica gel and eluted with $CHCl_3$. To provide a brown oil in 42% yield.

$^1$H-NMR (400 MHz, $CDCl_3$): δ 1.43 (s, 1H), 3.68 (t, J=7.6 Hz, 2H), 4.75 (t, J=7.6 Hz, 2H), 4.92 (bs, 1H), 7.51 (m, 2H), 7.09 (d, J=5.1 Hz, 1H), 7.99 (s, 1H), 9.60 (s, 1H). $^{13}$C-NMR (100 MHz, $CDCl_3$) δ 29.1, 38.4, 40.6, 80.7, 126.7, 127.5, 130.7, 132.1, 132.7, 133.8, 150.3, 157.3, 164.3.

N-(1-(2-aminoethyl)-1H-tetrazol-5-yl)-3-chlorobenzamide (D)

The BOC protected F2-derivative Compound (D) was added to a flask containing a 1:1 solution of $CH_2Cl_2$/TFA at room temperature. This solution was stirred for 5 hours upon which the solvent was evaporated under reduced pressure. The residual material was dissolved in $CH_2Cl_2$ and extracted with 0.1 M $NaHCO_3$, dried over anhydrous $MgSO_4$ and concentrated. Flash chromatography was performed using 98:2:0.1% ($CH_2Cl_2$:MeOH:$Et_3N$) to yield a brownish oil.

$^1$H-NMR (400 MHz, $CDCl_3$): δ 2.92 (bs, 2H), 3.62 (m, 2H), 4.69 (m, 2H), 7.48 (m, 2H), 7.11 (d, J=5.1 Hz, 1H), 7.95 (s, 1H), 9.80 (s, 1H). $^{13}$C-NMR (100 MHz, $CDCl_3$): δ47.3, 51.2, 125.4, 126.9, 129.4, 130.6, 132.2, 132.9, 148.7, 159.1

3-chloro-N-(1-(2-(5-(dimethylamino)naphthalene-1-sulfonamido)ethyl)-1H-tetrazol-5-yl)benzamide (E)

To a round bottom flask on ice (0° C.) was added the BOC-deprotected amine Compound (D) and $Et_3N$ dissolved in $CH_2Cl_2$. This mixture was stirred for 5 minutes after which a solution of dansyl chloride in $CH_2Cl_2$ was added dropwise over a period of 15 minutes.

The resulting reaction mixture was left to warm up to room temperature gradually and stirred continuously for 12 hours. A saturated solution of $NaHCO_3$ was added to the resulting composition that was thereafter extracted with $CH_2Cl_2$. The combined organic layer was dried over anhydrous $MgSO_4$ and concentrated in vacuo. Column chromatography performed on silica gel and elution with $CH_2Cl_2$ and a MeOH gradient of 1-5% gave a brownish solid in 70% yield.

$^1$H-NMR (400 MHz, $CDCl_3$): δ 2.90 (s, 6H), 3.47 (t, J=7.2 Hz, 2H), 4.51 (t, J=7.2 Hz, 2H), 6.40 (bs, 1H), 7.54 (m, 4H), 8.07 (m, 4H), 10.6 (bs, 1H). $^{13}$C-NMR (100 MHz, $CDCl_3$): δ41.6, 45.7, 48.3, 115.6, 119.0, 123.4, 123.5, 127.8, 128.8, 129.6, 129.7, 129.8, 130.2, 130.8, 131.2, 131.4, 134.2, 140.2, 152.2, 161.3, 171.4. ESI MS (+): m/z $[M+H]^+$500.2 (observed), calculated for $C_{22}H_{22}ClN_7O_3S$ 499.1.

Representative Synthetic Protocol for Compounds 1-8

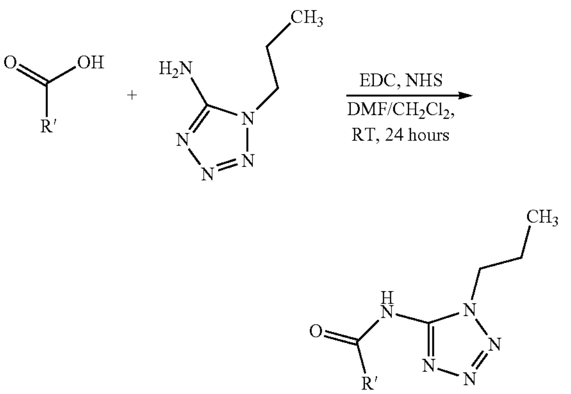

N-(1-propyl-1H-tetrazol-5-yl)benzamide (1)

(1)

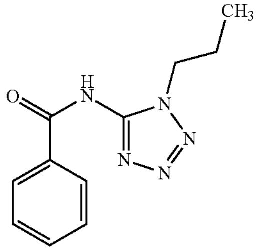

Employing 0.25 g (2.1 mmol) of benzoic acid and 0.26 g (2.1 mmol) of 1-propyl-1H-tetrazol-5-amine in the procedure described above for Compound F2 and elution with $CH_2Cl_2$/MeOH/$Et_3N$ (9.8:0.1:0.1) gave the product in 54% yield.

$^1$H-NMR (400 MHz, $CDCl_3$): δ 0.98 (t, J=7.4 Hz, 3H), 1.94 (q, J=7.4 Hz, 2H), 4.06 (t, J=7.4 Hz, 2H), 7.48 (m, 2H), 7.60 (t, J=6.0 Hz, 1H), 8.10 (d, J=7.3 Hz, 2H). $^{13}$C-NMR (100 MHz, $CDCl_3$): δ 10.1, 19.5, 43.4, 126.1, 128.2 131.1, 134.5, 158.1, 163.8.

3-bromo-N-(1-propyl-1H-tetrazol-5-yl)benzamide (2)

(2)

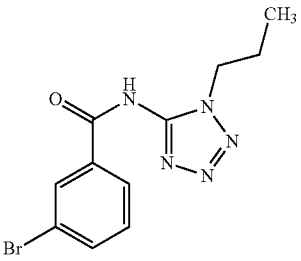

Employing 0.25 g (1.2 mmol) of 3-bromo-benzoic acid and 0.16 g (1.2 mmol) of 1-propyl-1H-tetrazol-5-amine in the procedure described above and elution with $CH_2Cl_2$/MeOH/$Et_3N$ (9.8:0.1:0.1) gave the product in 34% yield.

$^1$H-NMR (400 MHz, $CDCl_3$): δ 0.99 (t, J=7.5 Hz, 3H), 1.91 (q, J=7.5 Hz, 2H), 4.05 (t, J=7.1 Hz, 2H), 7.35 (t, J=7.8 Hz, 1H), 7.73 (d, J=7.9 Hz, 1H), 8.02 (d, J=7.8 Hz, 1H).). $^{13}$C-NMR (100 MHz, $CDCl_3$): δ 10.3, 23.5, 45.1, 121.1, 125.7, 127.7, 130.4, 133.9, 135.6, 159.8, 164.2.

3-fluoro-N-(1-propyl-1H-tetrazol-5-yl)benzamide (3)

(3)

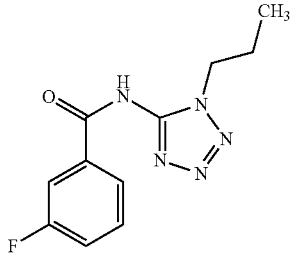

Employing 0.25 g (1.8 mmol) of 3-fluoro-benzoic acid and 0.23 g (1.8 mmol) of 1-propyl-1H-tetrazol-5-amine in the procedure described above and elution with $CH_2Cl_2$/MeOH/$Et_3N$ (9.8:0.1:0.1) gave the product in 52% yield.

$^1$H-NMR (400 MHz, $CDCl_3$): δ 0.89 (t, J=7.2 Hz, 3H), 1.85 (q, J=7.4 Hz, 2H), 4.03 (t, J=7.4 Hz, 2H), 7.02 (t, J=6.9 Hz, 1H), 7.26 (m, 1H), 7.58 (d, J=7.4 Hz, 1H), 7.69 (s, 1H). $^{13}$C-NMR (100 MHz, $CDCl_3$): δ 10.7, 25.1, 44.2, 123.5 124.9, 129.07, 131.3, 135.1, 146.2, 161.1, 165.9.

4-(dimethylamino)-N-(1-propyl-1H-tetrazol-5-yl) benzamide (4)

(4)

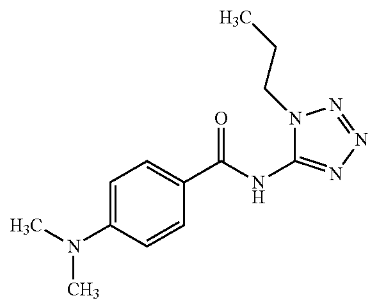

Employing 0.25 g (1.5 mmol) of 4-dimethyl-aminobenzoic acid and 0.19 g (1.5 mmol) of 1-propyl-1H-tetrazol-5-amine in the procedure described above and elution with $CH_2Cl_2$/MeOH/$Et_3N$ (9.6:0.2:0.2) gave the product in 46% yield.

$^1$H-NMR (400 MHz, $CDCl_3$): δ1.00 (t, J=7.4 Hz, 3H), 1.93 (q, J=7.4 Hz, 2H), 3.08 (s, 6H), 4.15 (t, J=7.4 Hz, 2H), 6.78 (d, J=8.7 Hz, 2H), 7.99 (d, J=8.7 Hz, 2H). $^{13}$C-NMR (100 MHz, $CDCl_3$) δ 10.1, 20.7, 31.2, 43.3, 114.8, 125.0, 131.1, 157.6, 159.1, 165.6.

4-(diethylamino)-N-(1-propyl-1H-tetrazol-5-yl)-benzamide (5)

(5)

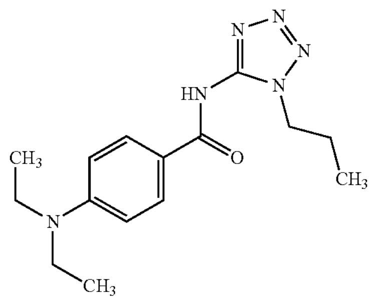

Employing 0.30 g (1.6 mmol) of 4-diethyl-aminobenzoic acid and 0.20 mg (1.6 mmol) of 1-propyl-1H-tetrazol-5-amine in the procedure described above and elution with $CH_2Cl_2$/MeOH/$Et_3N$ (9.6:0.2:0.2) gave the product in 56% yield.

$^1$H-NMR (400 MHz, $CDCl_3$): δ 1.00 (t, J=7.4 Hz, 3H), 1.21 (t, J=6.9 Hz, 3H), 1.90 (q, J=7.4 Hz, 2H), 3.44 (q, J=6.9 Hz, 4H), 4.05 (t, J=7.4 Hz, 2H), 6.63 (d, J=9.0 Hz, 2H), 7.94 (d, J=9.0 Hz, 2H). $^{13}$C-NMR (100 MHz, $CDCl_3$): δ 10.2, 11.4, 23.6, 39.8, 44.5, 112.6, 121.2, 130.4, 149.7, 155.9, 164.8.

3-chloro-N-(1-propyl-1-H-tetrazol-5-yl)benzamide (6)

(6)

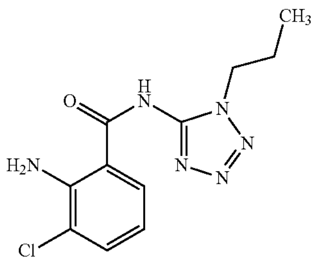

Employing 0.25 g (1.5 mmol) of 2-amino-3-chlorobenzoic acid and 0.19 g (1.5 mmol) of 1-propyl-1H-tetrazol-5-amine in the procedure described above and elution with $CH_2Cl_2$/MeOH/$Et_3N$ (9.4:0.3:0.3) gave the product in 65% yield.

$^1$H-NMR (400 MHz, $CDCl_3$): δ 0.99 (t, J=7.6 Hz, 3 H), 1.87 (q, J=7.6 Hz, 2H), 4.03 (t, J=7.4 Hz, 2H), 6.18 (s, 2H), 6.64 (t, J=8 Hz, 1H), 7.48 (d, J=8 Hz, 1H), 7.9 (d, J=8 Hz, 1H). $^{13}$C-NMR (100 MHz, $CDCl_3$): δ 11.7, 22.5, 39.6, 106.3, 116.3, 120.5, 130.0, 135.8, 147.8, 162.6, 169.5.

N-(1-propyl-1H-tetrazol-5-yl)cyclohexane-carboxamide (7)

(7)

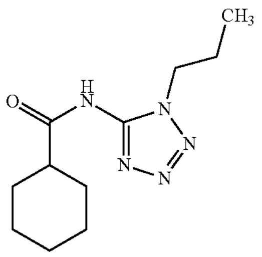

Employing 0.30 g (2.3 mmol) of cyclohexane carboxylic acid and 0.29 mg (2.3 mmol) of 1-propyl-1H-tetrazol-5-amine in the procedure described above and elution with $CH_2Cl_2$/MeOH/$Et_{31}$NT (9.3:0.5:0.2) gave the product in 49% yield.

$^1$H-NMR (400 MHz, $CDCl_3$): δ 0.97 (t, J=7.3 Hz, 3H), 1.27 (m, 3H), 1.42 (m, 2H), 1.65 (m, 3H), 1.92 (m, 3H), 2.30 (m, 1H), 4.14 (t, J=7.1 Hz, 2H), 8.82 (bs, 1H). $^{13}$C-NMR (100 MHz, $CDCl_3$): δ 11.2, 20.1, 26.3, 30.6, 41.2, 45.7, 156.8, 167.2.

N-(1-propyl-1H-tetrazol-5-yl)cyclopentane-carboxamide (8)

(8)

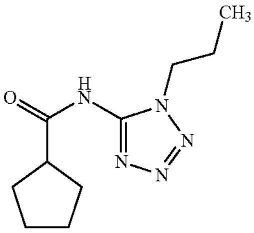

Employing 0.30 g (2.6 mmol) of cyclopentane carboxylic acid and 0.33 mg (2.6 mmol) of 1-propyl-1H-tetrazol-5-amine in the procedure described above and elution with $CH_2Cl_2$/MeOH/$Et_3N$ (9.3:0.5:0.2) gave the product in 45% yield.

$^1$H-NMR (400 MHz, $CDCl_3$): δ 0.98 (t, 3H), 1.56 (m, 2H), 1.67 (m, 4H), 1.77 (m, 2H), 1.88 (m, 4H), 2.60 (m, 1H), 4.10 (t, 2H), 9.42, (bs, 1H). $^{13}$C-

NMR (100 MHz, $CDCl_3$): δ 10.6, 21.8, 25.5, 29.6, 43.4, 46.6, 53.8, 172.1, 179.0.

Synthesis of 3-chloro-N-(1-propyl-1H-tetrazol-5-yl) benzamide (9)

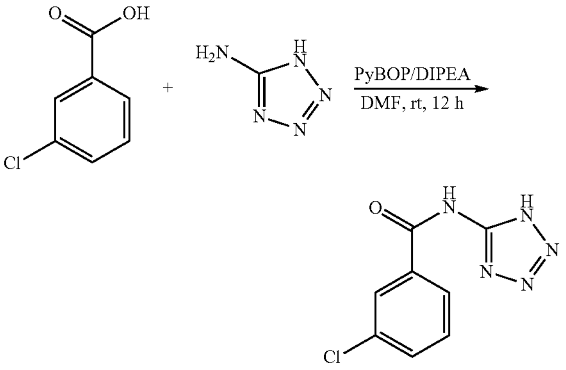

3-chloro-N-(1-propyl-1H-tetrazol-5-yl)benzamide (9)

A (9)

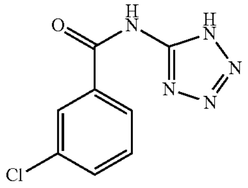

See the synthesis of Compound (A), above.

Synthesis of Compounds 10-13

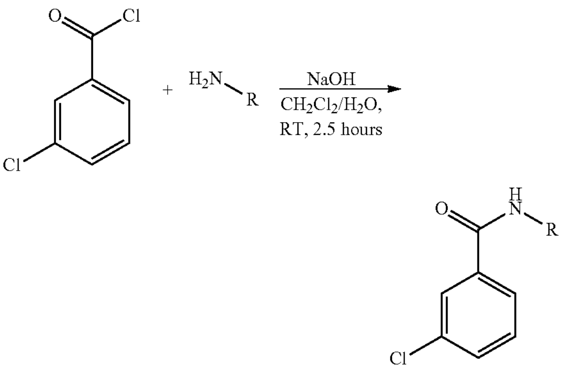

Representative Procedure:

3-chloro-N-phenylbenzamide (10)

(10)

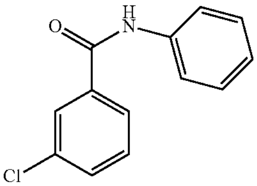

To a solution of aniline (178 mg, 1.9 mmol) in 20 mL $CH_2Cl_2$ at room temperature was added NaOH (76.2 mg, 2.9 mmol) in 6 mL water. This mixture was stirred vigorously for 5 minutes after which 3-chlorobenzoyl chloride (500 mg, 2.9 mmol) was added drop-wise while stirring over a period of 30 minutes. This reaction mixture was stirred for an additional 2 hours followed by an acid work-up and extraction with $CH_2Cl_2$ (3×20 mL). The organic layers were combined, dried over anhydrous $MgSO_4$. The product was purified via column chromatography on silica gel and eluted with a $CHCl_3$/MeOH/$Et_3N$ (9.8:0.1:0.1) to give white crystals in 81% yield.

$^1$H-NMR (400 MHz, $CDCl_3$): δ 7.18 (m, 1H), 7.38, (m, 3H), 7.51 (d, J=7.6 Hz, 1H), 7.63 (dd, J=6.6 Hz, 2H), 7.73 (d, J=7.6 Hz, 1H), 7.85 (bs, 1H), 7.93 (m, 1H). $^{13}$C-NMR (100 MHz, $CDCl_3$): δ 120.4, 124.9, 125.2, 127.4, 129.2, 130.1, 131.9, 135.0, 136.8, 137.6, 164.5.

3-chloro-N-(pyridin-4-yl)benzamide (11)

(11)

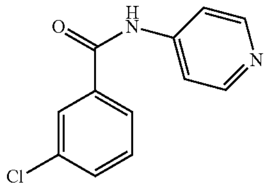

Employing 0.18 g (1.9 mmol) of 4-amino-pyridine and 0.51 g, (2.9 mmol) of 3-chlorobenzoyl chloride in the procedure described above and elution with $CHCl_3$/MeOH/$Et_3N$ (9.8:0.1:0.1) resulted in white crystals (52% yield).

$^1$H-NMR (400 MHz, $CDCl_3$): δ 6.92 (d, J=5.6 Hz, 1H), 7.41, (m, 3H), 7.55 (s, 1H), 8.34 (d, J=5.6 Hz, 2H), 8.48 (m, 2H), $^{13}$C-NMR (100 MHz, $CDCl_3$): δ 120.5, 125.0, 125.3, 127.5, 129.3, 130.3, 132.0, 161.3.

3-chloro-N-cyclohexylbenzamide (12)

(12)

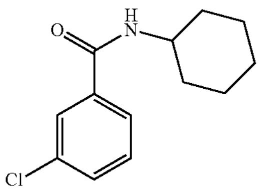

Employing 0.19 g (1.9 mmol) of cyclohexylamine and 0.51 g, (2.9 mmol) of 3-chloro-benzoyl chloride in the procedure described above and elution with $CHCl_3$/MeOH/$Et_3N$ (9.8:0.1:0.1) gave white crystals in 70% yield.

$^1$H-NMR (400 MHz, $CDCl_3$): δ 1.25 (m, 3H), 1.41 (m, 2H), 1.64 (m, 1H), 1.75, (m, 2H), 2.04 (m, 2H), 3.95 (m, 1H), 5.97 (s, 1H), 7.35 (m, 1H), 7.44 (d, J=8 Hz, 1H), 7.62 (d, J=8 Hz, 1H), 7.73 (s, 1H). $^{13}$C-NMR (100 MHz, $CDCl_3$): δ 24.9, 25.5, 33.2, 48.9, 125.0, 127.2, 129.9, 131.3, 134.7, 136.9, 165.3.

3-chloro-N-cyclopentylbenzamide (13)

(13)

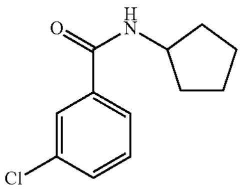

Employing 0.16 g (1.9 mmol) of cyclopentylamine and 0.51 g, (2.9 mmol) of 3-chloro-benzoyl chloride in the procedure described above and elution with $CHCl_3$/MeOH/$Et_3N$ (9.8:0.1:0.1) gave white crystals in 92% yield).

$^1$H-NMR (400 MHz, $CDCl_3$): δ 1.50 (m, 2H), 1.69 (m, 4H), 2.09 (m, 2H), 4.38 (m, 1H), 6.30 (s, 1H), 7.36 (m, 1H), 7.45 (d, J=8 Hz, 1H), 7.62 (d, J=8 Hz, 1H), 7.72 (s, 1H). $^{13}$C-NMR (100 MHz, $CDCl_3$): δ 23.6, 33.0, 51.7, 124.8, 127.0, 129.7, 131.1, 134.5, 136.6, 165.6.

3-chloro-N-(1-(2-(phenylsulfonamido)ethyl)-1H-tetrazol-5-yl)benzamide (16)

16

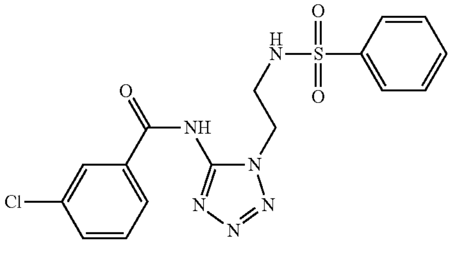

To a round bottomed flask at 0° C. was added Compound 4 (0.059 mmol, 1 eq) dissolved in 3 ml DCM and $Et_3N$ (0.179 mmol, 3 eq). Benzenesulfonyl chloride (0.079 mmol, 1.2 eq) dissolved in chilled DCM was then added dropwise over a period of 10 minutes. The reaction was stirred for an additional 20 minutes at 0° C. before being allowed to gradually warm to room temperature. The reaction was allowed to proceed for 12 hours at room temperature.

20 ml of DCM was then added to the crude solution followed by extraction with 0.1M $NaHCO_3$. The organic phase was dried over anhydrous $Na_2SO_4$ and concentrated in vacuo. The product was purified over silica gel and eluted with $CH_2Cl_2$:MeOH (1:1) to give a white powder in 70% yield.

$^1$H-NMR (400 MHz, DMSO-d6): δ 3.39 (t, J=7.6 Hz, 2H), 4.75 (t, J=7.6 Hz, 2H), 7.65 (m, 3H), 7.75 (d, J=7.2 Hz, 1H), 7.83 (d, J=7.9 Hz, 2H), 8.02 (m, 2H), 8.49 (s, 1H), 11.63 (s, 1H). $^{13}$C-NMR (100 MHz, DMSO-d6): 37.4, 40.3, 125.6, 127.5, 129.0, 130.2, 131.4, 131.9, 132.2, 134.4, 144.5, 156.1, 165.0.

Bacterial Strains and Culture Conditions

*B. anthracis* Sterne (pXO1+pXO2−) was propagated in Brain-Heart Infusion (BHI) medium (Sigma) and *S. aureus* strains were propagated in Tryptic Soy Broth (Hardy). Genetically modified *B. anthracis* Sterne strains were previously described in McGillivray et al., *J Innate Immun* 1:494-506 (2009). Clinical daptomycin nonsusceptible (DapNS)*S. aureus* clinical strains are described [Jones et al., *Antimicrob Agents Chemother* 52:269-278 (2008)], and DapNS MRSA strain SA32D was derived through in vitro passage [Sakoulas et al., *Antimicrob Agents Chemother* 50:1581-1585 (2006)].

Pulse-Chase Assays

The half-life of GFP with the *E. coli* tmRNA tag (GFP-AA) in vivo is determined using pulse chase assays [Keller et al., *Science* 271:990-993 (1996)]. *E. coli* cultures are grown in M9 minimal medium containing no methionine or cysteine at 30° C. to OD600=0.6, and GFP-AA expression is induced by the addition of isopropyl-1-thio-β-D-galactopyranoside (IPTG) to 1 mM. 90 Minutes after induction, cells are labeled with 30 μCi [$^{35}$S]L-methionine (MP Biomedicals) for 1 minute, and chased with a mixture of unlabeled L-methionine and L-cysteine at a final concentration of 1.25 mg/ml.

At each time point, 450 μl culture is removed and added to 50 μl trichloroacetic acid, and protein is recovered by centrifugation. Protein pellets are resuspended in 50 μl SDS buffer (10 mM Tris-HCl pH 8.0, 1% SDS, 1 mM EDTA), separated by gel electrophoresis on 15% SDS polyacrylamide gels, and the radiolabeled protein bands are visualized and quantified using a Typhoon™ imager (GE Healthcare Lifesciences). Half-lives are determined by fitting the plots of band intensity versus time to a single exponential. For cells treated with F2, F2 is added to 100 μM final concentration at the time of induction.

Bacterial Survival/Growth Assays

Cultures were grown to early log phase and resuspended to an optical density of 0.4 in PBS. *B. anthracis* Sterne is diluted 1:10 and *S. aureus* 1:100 in assay specific media to approximately $1\times10^6$ cfu/ml or $2\times10^6$ cfu/ml respectively and are grown for 24 hours at 37° C. under static conditions. Survival is measured by serial dilution and plating to enumerate surviving cfu/ml. Growth is measured by optical density at a wavelength of 600 nM. All studies are done at least 3 times and results from individual studies are combined and presented as mean+/−SEM.

F2 Resistance

Bacteria are grown overnight (about 18 hours) in the presence of 0 μM F2 (DMSO control) or 40 μM F2 in RPMI+5% LB. The next day the overnight cultures are diluted 1:100 (*B.

*anthracis*) or 1:1000 (*S. aureus*) in RPMI+5% LB and the indicated amount of F2 is added. Bacteria are then grown for an additional 24 hours in static conditions and surviving cfu/ml are enumerated.

Whole Blood Killing Assays

Blood collected from healthy donors (use and procedures approved by the University of California San Diego Human Research Protections Program) is incubated with 105 cfu *B. anthracis* and 40 μM F2 or vehicle control (DMSO) in a total volume of 500 μL and rotated at 37° C. At 30 minutes, a small aliquot is removed, blood was lysed in water and remaining bacteria are enumerated. Studies are performed using blood from three individual donors and results are combined and presented as mean+/−SEM.

Cytotoxicity Assay

HeLa cells are grown in Dulbecco's modified Eagle's medium (Difco)+10% fetal bovine serum (Invitrogen)+1% sodium pyruvate+1% penicillin/streptomycin (Difco). $2\times10^4$ Cells per well are plated in 96 well plates and grown for 24 hours at 37° C.+5% $CO_2$. Fresh medium containing the indicated concentration of F2 is added for an additional 24 hours. Zero μM F2 contains the equivalent vehicle control (DMSO) at the highest concentration. Untreated cells are included as a control. 20 μl of MTS tetrazolium from the CellTiter™ 96 AQueous One Solution Cell Proliferation Assay (Promega) is added to each well and incubated for 2 hours at 37° C.+5% $CO_2$ before quantifying absorbance at 490 nm. 100% Viability is set at the absorbance of the untreated cells. Two independent studies are combined and results are presented as mean+/−SEM.

Results

Inhibition of the ClpXP Protease.

The compound F2 was identified as part of a high-throughput screen for inhibitors of the protein tagging and degradation pathway known as trans-translation in *E. coli*. F2 inhibited proteolysis of ClpXp substrates in vivo using pulse chase assays that monitored the half-life of GFP with the *E. coli* tmRNA tag (GFP-AA). GFP-AA half-life was increased from 5.4+/−0.8 minutes to 18.7+/−5.7 minutes in the presence of F2. In comparison, bacteria lacking clpX had a protein half-life of 53.1+/−14 minutes (average half-life values from 3 studies).

ClpX/P are highly conserved among bacterial species [Chandu et al., *Res Microbiol* 155:710-719 (2004); Frees et al., *Microbiol* 63:1285-1295 (2007)] and therefore it is likely that a pharmacological inhibitor can function in multiple species. Genetic deletion of ClpX increases the susceptibility of *B. anthracis* Sterne to LL-37, the human cathelicidin antimicrobial peptide (see [McGillivray et al., *J Innate Immun* 1:494-506 (2009)].

Cathelicidins are critical first line effectors of innate defense against invasive bacterial infection [Nizet et al., *Nature* 414:454-457 (2001)]. It is hypothesized that if F2 could inhibit the ClpXp protease in *B. anthracis* Sterne, the parental bacteria would be rendered susceptible to cathelicidins in a manner similar to the mutant bacteria harboring a genetic deletion of the clpX gene.

At a dose of 40 μM, F2 alone did not affect *B. anthracis* Sterne growth. However, in combination with LL-37, growth is inhibited to the same level as the ΔclpX mutant.

To examine more precisely the interaction between F2 and LL-37 in killing *B. anthracis* Sterne, survival of the bacteria was assessed after 24 hour incubation with vehicle control, 40 μM F2 alone, 1.6 μM LL-37 alone, or a combination of 40 μM F2+1.6 μM LL-37. Incubation with either compound alone had a negligible effect on survival in comparison to the vehicle control, however when the two compounds were combined, recovery of *B. anthracis* cfu was below the limit of detection. Similar results were seen with murine cathelicidin, CRAMP.

The interaction between F2 and LL-37 was highly significant (two way ANOVA, P<0.0001), indicating a strong synergistic interaction between these two compounds [Slinker, *J Mol Cell Cardiol* 30:723-731 (1998). F2 functions in a dose-dependent manner because increasing amounts of F2 led to decreased bacterial survival when the amount of LL-37 is held constant.

To determine whether the synergistic effect of F2 and antimicrobial peptides on the bacteria could potentially be used in therapeutic treatment of infection, the ability of F2 to augment the bactericidal activity of human whole blood was assayed. Treatment of blood with 40 μM F2 significantly enhanced killing of *B. anthracis* in whole blood compared with the vehicle control. Cytotoxicity in mammalian cells was not seen until a dose of 500-1000 μM F2. Because the ClpXp protease plays a role in virulence in a number of pathogens, its inhibition could represent a potential therapeutic target for bacterial species besides *B. anthracis.*

*S. aureus* is a major human pathogen and a leading cause of skin, soft tissue and bloodstream infections. Of particular concern is the rise of antibiotic-resistant strains of *S. aureus* including methicillin-resistant *S. aureus* (MRSA) now epidemic in healthcare and community settings in the U.S. and other developed countries. Loss of ClpXp leads to decreased virulence of *S. aureus* and results in a number of shared phenotypes with *B. anthracis* including loss of hemolytic and proteolytic activity [Frees et al., *Mol Microbiol* 48:1565-1578 (2003); McGillivray et al., *J Innate Immun* 1:494-506 (2009)].

It was hypothesized that F2 may function in a similar manner in *S. aureus*, and F2 activity was assayed against several strains, including the methicillin-susceptible strain, Newman, and the MRSA strain, Sanger 252. In both cases survival of *S. aureus* was only slightly reduced when the bacteria were incubated for 24 hours with either 10 μM of LL-37 or 40 μM of F2 alone. However, combining LL-37 and F2 revealed a strong synergistic effect. No colonies were recovered for *S. aureus* Newman and survival was reduced by at least 10,000-fold for MRSA Sanger 252. F2 exhibits direct antimicrobial activity against *B. anthracis* Sterne and MRSA Sanger 252. Pre-treatment of bacteria with 40 μM F2 induces resistance in *S. aureus*, but not in *B. anthracis* under the same conditions.

Loss of ClpX Increases Susceptibility to Conventional Antibiotics.

Deletion of clpX in *B. anthracis* resulted in increased susceptibility to host defenses such as antimicrobial peptides and lysozyme that target components of the cell-envelope including the cell membrane and/or cell wall [McGillivray et al., *J Innate Immun* 1:494-506 (2009)]. Because these bacterial structures are also targets of certain classes of antibiotics, it was hypothesized that loss of clpX could increase susceptibility to cell envelope-acting antibiotics.

The parental *B. anthracis* Sterne, the ΔclpX mutant and the complemented strain ΔclpX+pclpX were incubated in media with or without 5 μg/ml of penicillin, a cell wall-acting antibiotic. It was found that although all three strains grew well in media without penicillin, growth of the ΔclpX mutant was significantly reduced in the presence of penicillin. Incubation with daptomycin, an antibiotic that disrupts membrane potential and causes cell-wall stress [Muthaiyan et al., *Antimicrob Agents Chemother* 52:980-990 (2008)], exerted a similar effect.

No viable bacteria were recovered upon incubation of the ΔclpX mutant with daptomycin, whereas the parental and the complemented strains were not significantly affected by daptomycin. This effect is not seen with all antibiotics as no differences in growth were seen upon incubation with either ciprofloxacin, which targets topoisomerase II, or erythromycin, which targets protein synthesis.

Inhibition of ClpXP Increases Antibiotic Sensitivity

Because ClpX was important for resistance to penicillin and daptomycin in *B. anthracis* Sterne, whether inhibition of the ClpXP protease using F2 would sensitize *B. anthracis* Sterne to penicillin or MRSA Sanger 252 to daptomycin was next assayed. Bacteria were incubated with vehicle control, F2 alone, antibiotic alone, or a combination of F2+antibiotic. Bacterial survival (cfu/ml) was determined at 24 hours.

In both cases, neither treatment with F2 nor antibiotic alone had a significant effect on survival. However, a combination of F2 and penicillin with *B. anthracis* Sterne or F2 and daptomycin with MRSA significantly reduced bacterial survival in a synergistic manner. Although daptomycin is a relatively new antibiotic, resistant strains have already been reported in clinical practice [Hayden et al., *J Clin Microbiol* 43:5285-5287 (2005); Sakoulas et al., *J Clin Microbiol* 46:220-224 (2008)].

Whether F2 could increase daptomycin susceptibility (DapS) in daptomycin-non-susceptible (DapNS) *S. aureus* strains was queried next. Strains SA0616 (DapS) and SA0701 (DapNS) were isolated from the bloodstream of a patient with daptomycin treatment failure before and after daptomycin therapy [Sakoulas et al., *J Clin Microbiol* 46:220-224 (2008)]. DapNS MRSA strain SA32D was derived by in vitro passage of DapS MRSA strain SA32 (25). Both SA0701 and SA32D were more resistant to daptomycin killing than their parental strains, SA0616 and SA32 respectively. Also, in both cases, treatment of either SA0701 or SA32D with F2 decreased their resistance to daptomycin, although in neither case did it return daptomycin susceptibility to its original levels.

Cellular Localization of Dansyl-F2 in *B. anthracis* Sterne

An overnight (about 18 hours) culture of *B. anthracis* Sterne was inoculated to a starting $OD_{600}$ of 0.02 in fresh LB growth medium. This culture was then transferred into plastic tubes each holding 0.5 ml. Dansyl-F2 was added to duplicate tubes to a final concentration of 3 μM. Assay tubes were incubated at 37° C. for 6 hours after which cells were pelleted, washed once with medium without dansyl-F2, and then resuspended in 100 μl of LB. An aliquot (5 μl) of the thus prepared composition was placed on an agar pad for visualization.

Fluorescence images were obtained on a Eclipse 90i microscope (Nikon) using a 60×TIRF N. A. 1.4 oil immersion objective and a Nikon CoolSNAP HQ CCD camera controlled by simple PCi (Compix, Inc.) Those images showed the fluorescent compound within the bacterial cells.

*B. anthracis* Sterne Spore Preparation

Following the procedures of Alvarez et al., *Antimicrob. Agents and Chem.* 2010 54:5329-5336, an overnight (about 18 hours) *B. anthracis* Sterne culture was plated on plain LB Agar plates which were then incubated at 37° C. for 5 days to obtain bacterial lawns. The resulting lawns were collected by flooding with sterile ice cold deionized water. This suspension was pelleted by centrifugation (4° C.) at 10,000 rpm for 10 minutes. Spores were then washed three times with fresh ice cold deionized water, pelleted by centrifugation and resuspended in the same medium. Spores were incubated at 70° C. for 30 min to kill any vegetative cells followed by storage at 4° C. in sterile deionized water. Spore viability was assessed by plating the heat-treated spores on plain LB agar plates and monitoring spore germination by microscopy.

Activation of *B. anthracis* Sterne Spore Germination

*B. anthracis* Sterne spores were activated and germinated following literature procedures. (Alvarez et al., *Antimicrob. Agents and Chem.* 2010 54:5329-5336; and Akochere et al., J. Biol. Chem. 2007 282:12112-12118). Thus, prior to starting an assay spore suspensions were heat activated at 70° C. for 30 minutes. Germination was achieved by resuspension in 50 mM Tris-HC1 [pH 7.5], 10 mM NaCl supplemented with L-alanine (40 μM) and inosine (250 μM). Spore suspensions were analyzed for auto-germination in the absence of L-alanine and inosine. No vegetative cells were observed under the microscope.

Germination was monitored spectrophotometrically and using microscopy. Spectrophotometrically, loss in light diffraction following addition of germinants was indicated by a decrease in optical density at 580 nm. Microscopic analyses were performed on a Nikon Eclipse E600 and were used to identify the presence of vegetative cells following incubation. Typically, 0.5 ml assay volumes were used with at least duplicate set-ups. Germination was performed in a 37° C. shaker. At a desired time point an aliquot (5 ml) was transferred onto an agar pad and visualized under the microscope for signs of germination.

Inhibition of *B. anthracis* Spore Germination

Inhibition of spore germination was assayed using a similar protocol as that described above. Immediately following addition of the germinants (L-alanine and inosine) into the germination buffer, 500 μl samples were transferred into tubes containing a pre-calculated concentration of the desired test compound. Samples were analyzed at a desired time point 0-48 hours by microscopy.

Each of the patents and articles cited herein is incorporated by reference.

The foregoing description and the examples are intended as illustrative and are not to be taken as limiting. Still other variations within the spirit and scope of this invention are possible and will readily present themselves to those skilled in the art.

The invention claimed is:

1. A compound of structural Formula I or a pharmaceutically acceptable salt of that compound

I

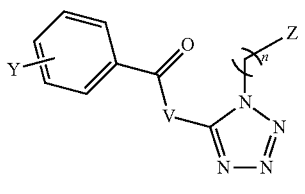

wherein n is 1-6;

V is O or $NR^9$;

$R^9$ is hydrido (H) or $C_1$-$C_4$ hydrocarbyl;

Z is $NR^2$—X—$R^1$ or $CH_2$—$R^8$;

X is hydrido (H), $S(O)_2$, C(O), $C(O)NR^7$, $C(NH)NR^7$ or C(O)O, with the proviso that when X is H, $R^1$ and $CH_2$—$R^8$ are absent;

Y is halogen, $OR^{10}$, $C_1$-$C_4$ hydrocarbyl or $NHR^{10}$;

$R^{10}$ is hydrido or $C_1$-$C_4$ hydrocarbyl;

$R^1$ and $R^8$ are the same or different and are an aliphatic, aromatic or heteroaromatic ring system containing one ring or two fused rings each having 5-7 atoms in the ring, said ring system containing up to three substituents other than hydrogen that themselves can be the same or different ($R^{1a}$, $R^{1b}$, and $R^{1c}$), and wherein each of those three groups, $R^{1a-c}$, is separately selected from the group consisting of $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl, hydroxy-, halogen, halogen-substituted $C_1$-$C_7$ hydrocarboyl, $C_1$-$C_6$ hydrocarbylsulfonyl, $C_1$-$C_6$ hydrocarbyloxysulfonyl, nitro, phenyl, benzyl, cyano, carboxyl, $C_1$-$C_7$ hydrocarbyl carboxylate, carboxamide or sulfonamide wherein the amido nitrogen in either group has the formula $NR^3R^4$ in which $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N═N— and Ar is a single-ringed aryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur; and $R^2$ and $R^7$ are the same or different and are hydrido or $C_1$-$C_4$ hydrocarbyl.

2. The compound or pharmaceutically acceptable salt according to claim 1, wherein n is 2-4.

3. The compound or pharmaceutically acceptable salt according to claim 1, wherein Z is $NR^2$—X—$R^1$.

4. A compound of structural Formula IIA or a pharmaceutically acceptable salt of that compound

IIA

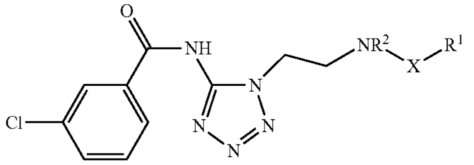

wherein

X is $S(O)_2$, C(O), $C(O)NR^7$, $C(NH)NR^7$ or C(O)O;

$R^1$ is an aliphatic, aromatic or heteroaromatic ring system containing one ring or two fused rings each having 5-7 atoms in the ring, said ring system containing up to three substituents other than hydrogen that themselves can be the same or different ($R^{1a}$, $R^{1b}$, and $R^{1c}$), and wherein each of those three groups, $R^{1a-c}$, is separately selected from the group consisting of $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl, hydroxy-, halogen, halogen-substituted $C_1$-$C_7$ hydrocarboyl, $C_1$-$C_6$ hydrocarbylsulfonyl, $C_1$-$C_6$ hydrocarbyloxysulfonyl, nitro, phenyl, benzyl, cyano, carboxyl, $C_1$-$C_7$ hydrocarbyl carboxylate, carboxamide or sulfonamide wherein the amido nitrogen in either group has the formula $NR^3R^4$ in which $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N═N— and Ar is a single-ringed aryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur; and $R^2$ and $R^7$ are the same or different and are hydrido or $C_1$-$C_4$ hydrocarbyl.

5. The compound or pharmaceutically acceptable salt according to claim 4, wherein X is C(O) or $S(O)_2$.

6. The compound or pharmaceutically acceptable salt according to claim 5, wherein $R^1$ is an aromatic or heteroaromatic ring system.

7. The compound or pharmaceutically acceptable salt according to claim 5, wherein $R^2$ is hydrido.

8. The compound or pharmaceutically acceptable salt according to claim 5, wherein said compound of Formula IIA has the structural formula

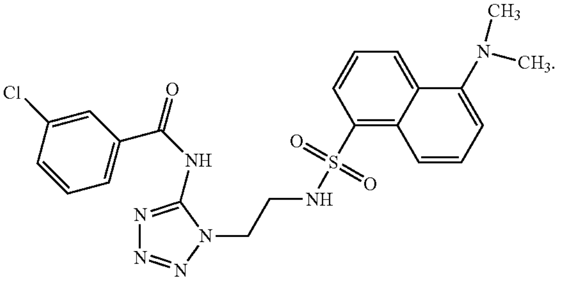 [SMILES: CN(C)c1cccc2c(S(=O)(=O)NCCn3nnnc3NC(=O)c3cccc(Cl)c3)cccc12]

9. A pharmaceutical composition that comprises a bactericidal or bacteriostatic amount of a compound or its pharmaceutically acceptable salt of claim 1 dissolved or dispersed in a pharmaceutically acceptable diluent.

10. A method of inhibiting the growth of bacteria that comprises the steps of contacting said bacteria with an antibacterial amount of a compound or its pharmaceutically acceptable salt of claim 1.

11. The method according to claim 10, wherein said bacteria are contacted a plurality of times.

12. The method according to claim 10, wherein said bacteria are Gram positive.

13. The method according to claim 12, wherein said Gram positive bacteria are *B. anthracis.*

14. The method according to claim 12, wherein said Gram positive bacteria are *S. aureus.*

15. The method according to claim 14, wherein said Gram positive bacteria are *M. tuberculosis.*

16. The method according to claim 10, wherein said bacteria are Gram negative.

17. The method according to claim 10 wherein said bacteria are present in a cell culture.

18. The method according to claim 10 wherein said bacteria are present in an infected mammal and said bacteria are contacted by administration of said compound to said infected mammal.

19. The method according to claim 10, wherein said compound has the structural formula

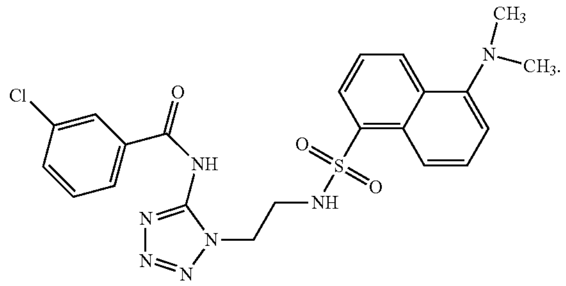 [SMILES: CN(C)c1cccc2c(S(=O)(=O)NCCn3nnnc3NC(=O)c3cccc(Cl)c3)cccc12]

20. A method of inhibiting the growth of bacteria that comprises the steps of contacting said bacteria with a synergistic amount of a compound or its pharmaceutically acceptable salt of claim 1 and a synergistic amount of a) a human cathelicidin antimicrobial peptide LL-37 or b) an antibiotic that targets the cell wall and/or the cell membrane.

21. The method according to claim 20, wherein said bacteria are Gram positive.

22. The method according to claim 20, wherein said bacteria are Gram negative and an effective amount of an efflux system-impairing drug is administered.

23. The method according to claim 20, wherein said compound has the structural formula

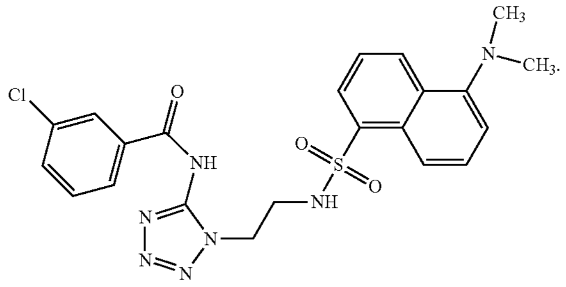 [SMILES: CN(C)c1cccc2c(S(=O)(=O)NCCn3nnnc3NC(=O)c3cccc(Cl)c3)cccc12]

* * * * *